US008741580B2

(12) United States Patent
Kienle et al.

(10) Patent No.: US 8,741,580 B2
(45) Date of Patent: Jun. 3, 2014

(54) MARKERS OF RENAL TRANSPLANT REJECTION AND RENAL DAMAGE

(75) Inventors: Stefan Kienle, Frankfurt am Main (DE); Richard Joubert, Frankfurt am Main (DE)

(73) Assignee: Electrophoretics Limited, Surrey (GB)

( * ) Notice: Subject to any disclaimer, the term of this patent is extended or adjusted under 35 U.S.C. 154(b) by 0 days.

(21) Appl. No.: 13/237,146

(22) Filed: Sep. 20, 2011

(65) Prior Publication Data

US 2012/0065095 A1 Mar. 15, 2012

Related U.S. Application Data

(62) Division of application No. 11/850,231, filed on Sep. 5, 2007, now Pat. No. 8,021,895.

(30) Foreign Application Priority Data

Sep. 5, 2006 (GB) .................................. 0617429.6

(51) Int. Cl.
G01N 33/53 (2006.01)
(52) U.S. Cl.
CPC ............. G01N 33/53 (2013.01); Y10S 436/811 (2013.01)
USPC ............ 435/7.1; 435/7.92; 436/518; 436/811

(58) Field of Classification Search
None
See application file for complete search history.

(56) References Cited

U.S. PATENT DOCUMENTS

| 6,329,209 | B1 | 12/2001 | Wagner et al. |
| 6,974,704 | B2 | 12/2005 | Nelson et al. |
| 7,067,634 | B2 | 6/2006 | Tomita et al. |

OTHER PUBLICATIONS

Strongin, Laboratory Diagnosis of Viral Infections, Sensitivity, Specificity, and Predictive Value of Diagnostic Tests: Definitions and Clinical applications, Lennette, ed. Marcel Dekker, Inc. New York, pp. 211-219, 1992.*
Paul., Chronic allograft nephropathy: An update, Kidney International, vol. 56 (1999), pp. 783-793.*
Bast et al. "Translational Crossroads for Biomarkers" Clin Cancer Res 2005; 11(17), 6103-6108.*
LaBaer et al. "So, You Want to Look for Biomarkers" Journal of Proteome Research 2005; 4, 1053-1059.*
Baker "In Biomarkers We Trust?" Nature Biotechnology 2005; 23(3), 297-304.*
L. Backman et al., "Serum levels of alpha-1 microglobulin in recipients of renal allografts", Transpl. Int., 2(1): 23-26 (1989).
N. Cano, "Metabolism and Clinical Interest of Serum Transthyretin (Prealbumin) in Dialysis Patients", Clin. Chem. Lab. Med., 40(12): 13131-1319 (2002).

P. Chowdhury et al., "Complement in Renal Transplantation", Nephron. Clin. Pract., 95: c3-c8 (2003).
W. Clarke et al., "Proteomic Research in Renal Transplantation", Ther. Drug. Monit., 28: 19-22 (2006).
W. Clarke et al., "Characterization of Renal Allograft Rejection by Urinary Proteomic Analysis", Annals of Surgery, 237(5): 660-665 (2003).
P. Cutillas et al., "Proteomic Strategies and Their Application in Studies of Renal Function", News Physiol. Sci., 19: 114-119 (2004).
S. Jain et al., "Proteomic Analysis of Urinary Protein Markers for Accurate Prediction of Didabetic Kidney Disorder", JAP1, 53: 513-520 (2005).
F. Kronenberg et al., "Apolipoprotein A-IV Serum Concentrations Are Elevated in Patients with Mild and Moderate Renal Failure", J. Am. Soc. Nephrol., 13: 461-469 (2002).
M. Lapsley et al., "B2-Glycoprotein-1 (apolipoprotein H) excretion and renal tubular malfunction in diabetic patients without clinical proteinuria", J. Clin. Pathol., 46: 465-469 (1993).
M. Nguyen et al., "Early Prediction of Acute Renal Injury Using Urinary Proteomics", Am. J. Nephrol., 25: 318-326 (2005).
K. Opatrny Jr. et al., "Fibrinolysis in Chronic Renal Failure, Dialysis and Renal Transplantation", Annals of Transplantation, 7(1): 34-43 (2002).
S. Sacks et al., "Role of the complement system in rejection", Current Opinion in Immunology, 15: 487-492 (2003).
S. Sacks et al., "The effect of locally synthesised complement on acute renal allograft rejection", J. Mol. Med., 81: 404-410 (2003).
S. Sacks et al., "Locally Produced Complement and its Role in Renal Allograft Rejection", American Journal of Transplantation 3: 927-932 (2003).
V. Thongboonkerd et al., "Renal and urinary proteomics: Current applications and challenges", Proteomics, 5: 1033-1042 (2005).
L.A. Trouw et al., "Complement and renal disease", Molecular Immunology, 40: 125-134 (2003).
S. Vaidya et al., "Role of anti-B 2 glycoprotein 1 antibodies in ESRD patients with antiphospholipid antibody syndrome", Clin. Transplant., 16: 362-367 (2003).
B. Vidal Jr. et al., "Towards the application of proteomics in renal disease diagnosis", Clinical Science, 109: 421-430 (2005).
H. Voshol et al., "Evaluation of Biomarker Discovery Approaches to Detect Protein Biomarkers of Acute Renal Allograft Rejection", Journal of Proteome Research, 4: 1192-1199 (2005).
Y. Wang et al., "Expression of tissue type plasminogen activator and type 1 plasminogen activator inhibitor, and persistent fibrin deposition in chronic renal allograft failure", Kidney International, 52: 371-377 (1997).
S. Wittke et al., "Detection of Acute Tubulointerstitial Rejection by Proteomic Analysis of Urinary Samples in Renal Transplant Recipients", American Journal of Transplantation, 5: 2479-2488 (2005).
C. Zoccali et al., "Inflammatory proteins as predictors of cardiovascular disease in patients with end-stage renal disease", Nephrol. Dial. Transplant., 19: v67-v72 (2004).

* cited by examiner

Primary Examiner — Gary W Counts
(74) Attorney, Agent, or Firm — Patrick J. Hagan; Dann, Dorfman, Herrell and Skillman, P.C.

(57) ABSTRACT

The present invention relates to methods of detecting renal transplant rejection and other forms of renal damage. Protein markers or renal damage are provided, along with assays for detecting said markers. Also provided are methods for identifying markers of renal damage.

10 Claims, 24 Drawing Sheets

MARKERS OF RENAL TRANSPLANT REJECTION AND RENAL DAMAGE

CROSS-REFERENCE TO RELATED APPLICATIONS

This application is a divisional of U.S. patent application Ser. No. 11/850,231, filed Sep. 5, 2007 (now U.S. Pat. No. 8,021,895). The entire disclosure of the aforesaid application is incorporated by reference in the present application.

FIELD OF THE INVENTION

The present invention relates to methods of detecting renal transplant rejection and other forms of renal damage.

BACKGROUND TO THE INVENTION

Allograft rejection constitutes the major impediment to the success of renal transplantation. Chronic rejection is currently the most prevalent cause of renal transplant failure. Clinically, chronic rejection presents by chronic transplant dysfunction, characterized by a slow loss of function, often in combination with proteinuria and hypertension. Chronic rejection develops in grafts that undergo intermittent or persistent damage from cellular and humoral responses resulting from indirect recognition of alloantigens. The most effective option to prevent renal failure from chronic rejection is to avoid graft injury from both immune and nonimmune mechanism together with nonnephrotoxic maintenance immunosuppression. Currently available diagnostic methods, including clinical presentation and biochemical organ function parameters, often fail to detect rejection until late stages of progression.

SUMMARY OF THE INVENTION

The inventors have identified biomarkers for detection of renal allograft rejection and other forms of renal damage. The invention relates to diagnosis and treatment of renal damage, including renal transplant allograft rejection, using these biomarkers. Use of the biomarkers includes use or detection of the proteins identified or fragments thereof, nucleic acids encoding said proteins or the complement thereof, and antibodies binding to said proteins.

Thus, the invention provides the use of the presence or amount of a protein set out in Table 4 or Table 5 or a fragment thereof, or antibodies against said proteins, or nucleic acids encoding said proteins or fragments thereof, as a marker for the diagnosis and/or prognosis of renal damage. Also provided is a method for the diagnosis and/or prognosis of renal damage, the method comprising determining the presence or amount of a protein set out in Table 4 or Table 5, or a fragment thereof, or antibodies against said proteins, or nucleic acids encoding said proteins or fragments thereof in a sample from a patient.

Also provided is the use of a protein set out in Table 4 or Table 5 or a fragment thereof, an antibody against one of said proteins, a nucleic acids encoding said proteins or a fragment thereof, or a nucleic acid which is the complement of a nucleic acids encoding said proteins or a fragment thereof, in a method of diagnosis or prognosis of renal damage.

In some embodiments, prognosis and/or diagnosis is prognosis and/or diagnosis of chronic rejection following renal transplantation, also known as chronic allograft nephropathy (CAN). In other embodiments, prognosis and/or diagnosis may be prognosis and or diagnosis of renal damage caused by disease or toxicity, for example In one embodiment, the method comprises the steps of:
(a) contacting a sample from a patient with a solid support having immobilised thereon a binding agent having binding sites which are capable of specifically binding to the marker protein, antibody or nucleic acid with a sample from a patient under conditions in which the marker protein, antibody or nucleic acid bind to the binding agent; and,
(b) determining the presence or amount of the marker protein, antibody or nucleic acid bound to the binding agent.

Step (b) may comprise (i) contacting the solid support with a developing agent which is capable of binding to occupied binding sites, unoccupied binding sites or the marker protein, antibody or nucleic acid, the developing agent comprising a label and (ii) detecting the label to obtain a value representative of the presence or amount of the marker protein, antibody or nucleic acid in the sample.

The label may be, for example, a radioactive label, a fluorophor, a phosphor, a laser dye, a chromogenic dye, a macromolecular colloidal particle, a latex bead which is coloured, magnetic or paramagnetic, an enzyme which catalyses a reaction producing a detectable result or the label is a tag.

In some embodiments, the binding agent is a protein set out in Table 4 or Table 5, or a fragment thereof. In other embodiments, the binding agent is an antibody which is capable of binding to a protein set out in Table 4 or Table 5, or a fragment thereof. In other embodiments, the binding agent may be a nucleic acid which is complementary to the sequence of the nucleic acid to be detected.

In an alternative embodiment, the method comprises detecting a marker protein or marker proteins in a sample from a patient using mass spectroscopy. The proteins in the sample may be immobilised on a solid support. Optionally, the proteins may be subjected to proteolytic digestion prior to analysis. Suitable analytical methods include SELDI-TOF and MRM.

In some embodiments, the method comprises determining the presence or amount of a plurality of marker proteins, antibodies or nucleic acids associated with renal damage in a single sample. For example, a plurality of binding agents may be immobilised as predefined locations on the solid support.

Also provided is a kit for use in the diagnosis or prognosis of renal damage by determining the presence or amount of an analyte selected from a protein set out in Table 4 or Table 5 or a fragment thereof, an antibody against said protein, and a nucleic acid encoding said protein or a fragment thereof, in a sample from a patient, the kit comprising:
(a) a solid support having a binding agent capable of binding to the analyte immobilised thereon;
(b) a developing agent comprising a label; and,
(c) one or more components selected from the group consisting of washing solutions, diluents and buffers. The binding agent may be as defined above. In particular, for detection of an autoantibody, the binding agent may be a protein set out in Table 4 or Table 5, or a fragment thereof. For detection of a marker protein, the binding agent may be an antibody which is capable of binding to a protein set out in Table 4 or Table 5, or a fragment thereof. For detection of a nucleic acid, the binding agent may be a nucleic acid which is complementary to the sequence of the nucleic acid to be detected.

Also provided is a kit for use in the diagnosis or prognosis of renal damage by determining the presence or amount of an analyte selected from a protein set out in Table 4 or Table 5, in a sample from a patient, the kit comprising one or more MRM peptides, as described below, in an assay-compatible format.

Also provided is the use of a protein set out in Table 4 or Table 5, or a fragment thereof, or antibodies capable of specifically binding these proteins, for the preparation of a medicament for the treatment of renal damage.

Further provided is the use of the presence or amount of a nucleic acid encoding any one of the proteins set out in Table 4 or Table 5 or a fragment thereof as a marker for the diagnosis and/or prognosis of renal damage.

In one embodiment, the invention provides a method for the diagnosis and/or prognosis of renal damage, the method comprising determining the presence or amount of a nucleic acid encoding any one of the proteins set out in Table 4 or Table 5, or a fragment thereof, in a sample from a patient.

Also provided is a kit for use in the diagnosis or prognosis of chronic renal transplant rejection by determining the presence or amount of an analyte selected from a protein set out in Table 4 or Table 5, or a fragment thereof, or antibodies against these antigens, in a sample from a patient, the kit comprising:
  (a) a solid support having a binding agent capable of binding to the analyte immobilised thereon;
  (b) a developing agent comprising a label; and,
  (c) one or more components selected from the group consisting of washing solutions, diluents and buffers.

Renal damage may include chronic rejection following renal transplantation, also known as chronic allograft nephropathy, or renal damage caused by disease or toxicity.

The methods of the invention are in most cases in vitro methods carried out on a sample from a patient. The sample used in the methods described herein may be a tissue or body fluid sample, for example a renal tissue sample, a blood or blood product (such as serum or plasma) sample or a urine sample. In a preferred embodiment, the sample is a depleted sample, i.e. a sample from which highly abundant proteins have been removed or depleted.

In preferred embodiments, said marker protein is any one of N-acetylmuramoyl-L-alanine amidase precursor, adiponectin, AMBP protein precursor ($\alpha_1$-microglobulin), C4b-binding protein $\alpha$-chain precursor, ceruloplasmin precursor, complement C3 precursor, complement component C9 precursor, complement factor D precursor, $\alpha_{1B}$-glycoprotein, $\beta_2$-glycoprotein I precursor, heparin cofactor II precursor, Ig $\mu$ Chain C region protein, Leucine-rich $\alpha_2$-glycoprotein precursor, pigment epithelium-derived factor precursor, plasma retinol-binding protein precursor and translation initiation factor 3 subunit 10.

DETAILED DESCRIPTION

Renal Damage

Figure 1:
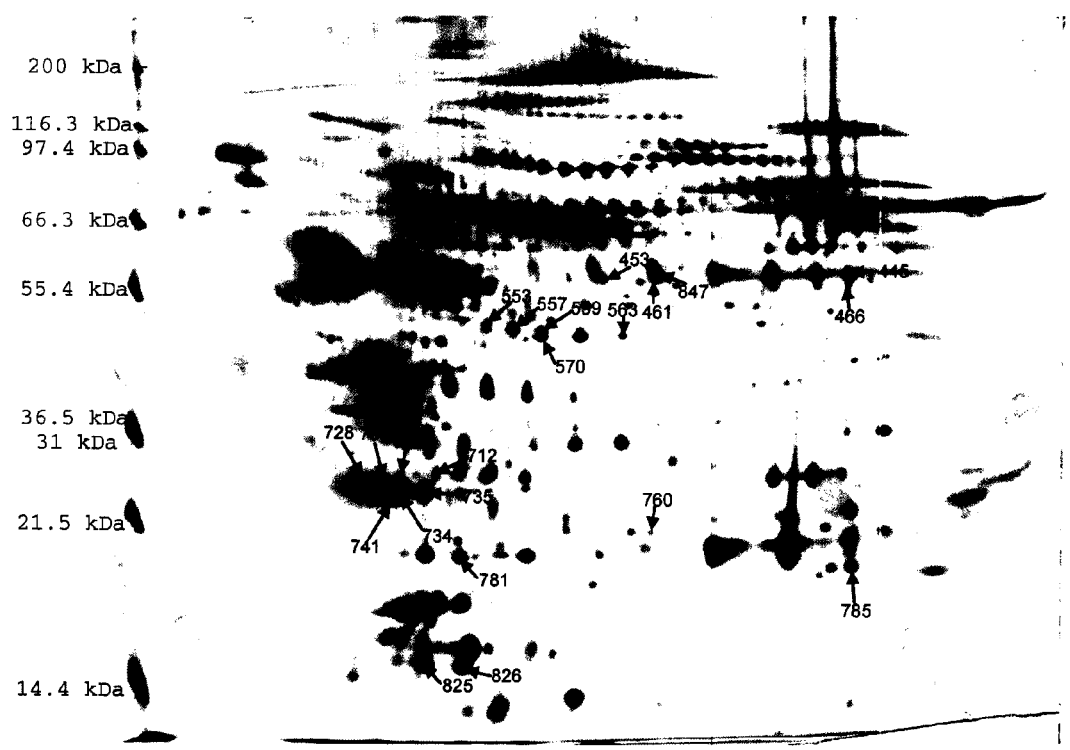
FIG. 1 Analytical 2D-gel of serum sample C51-1 (comparison C1 vs. C3)
Figure 2:
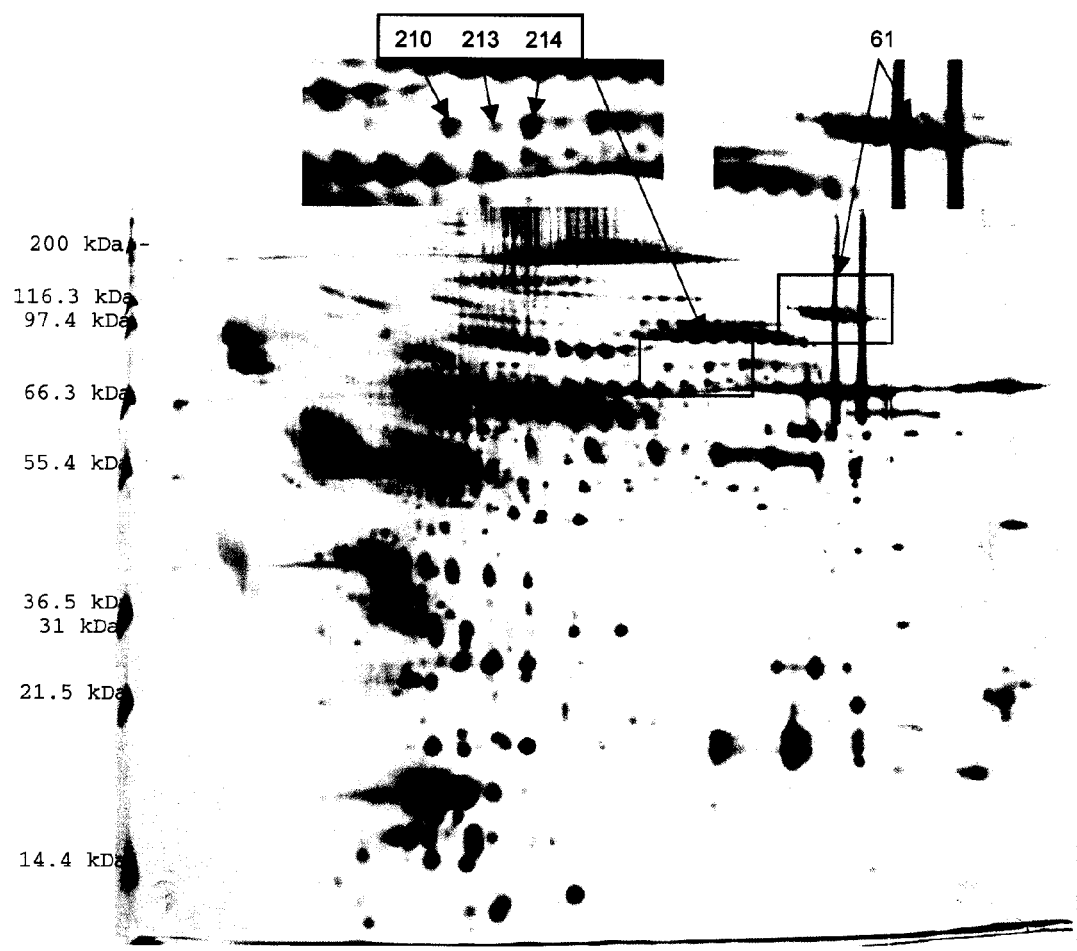
FIG. 2 Analytical 2D-gel of serum sample C51-1 (comparison C1 vs. C3)
Figure 3:
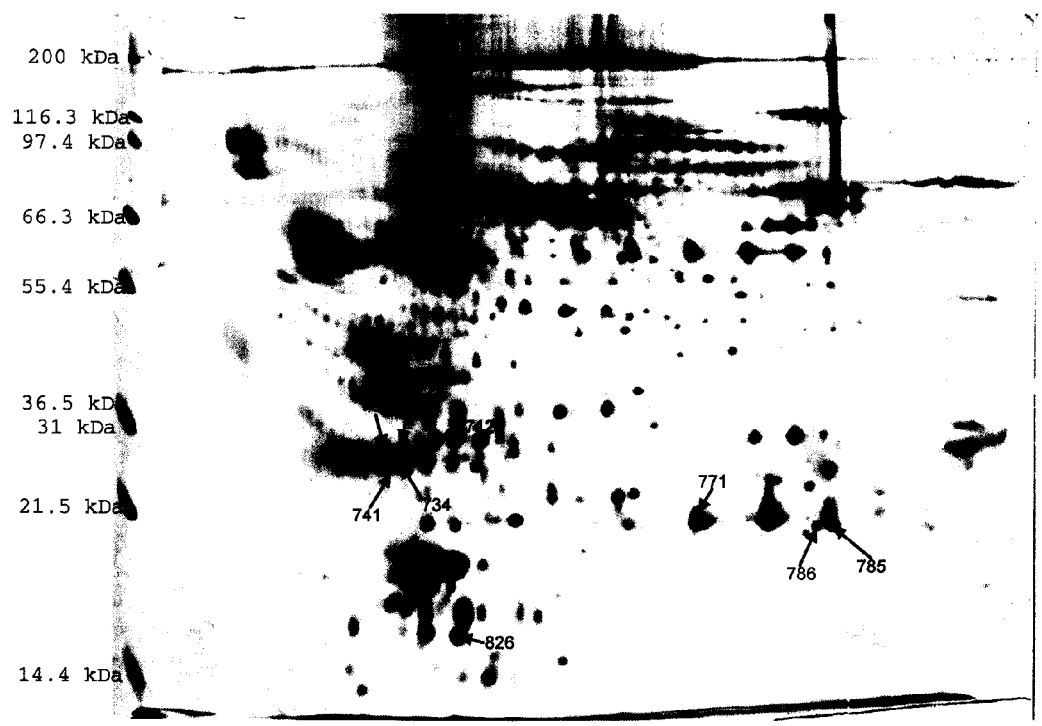
FIG. 3 Analytical 2D-gel of serum sample D12-1 (comparison D1 vs. D3)
Figure 4:
FIG. 4 Preparative 2D-gel of pooled control samples of study group
Figure 5:
FIG. 5 Preparative 2D-gel of pooled disease samples of study group
Figure 6:
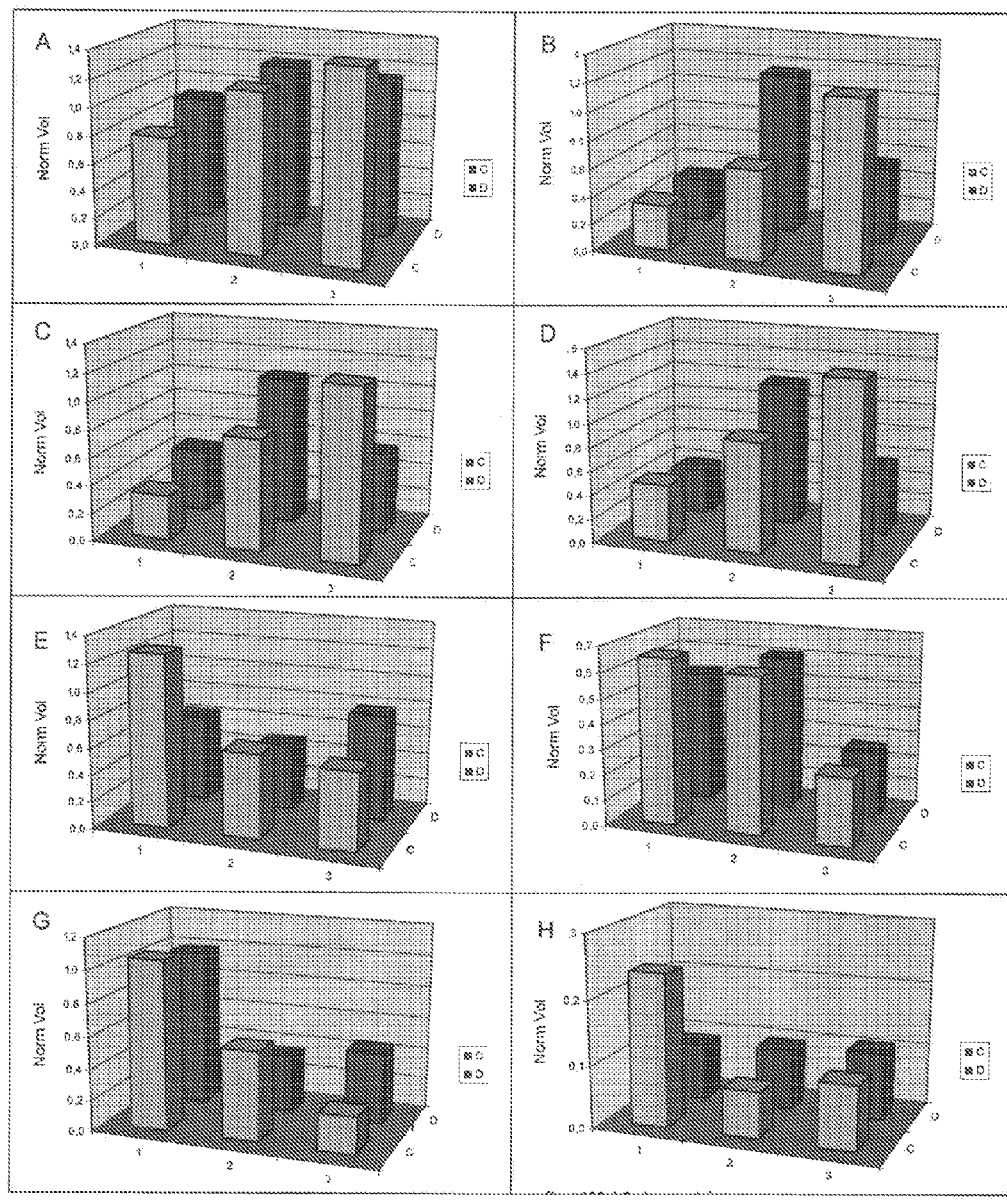
FIG. 6 Histograms of the time course of protein regulations from disease (dark grey) and control (light grey) samples of table 4 at timepoints 1, 2 and 3. Vertical axis: normalised spot volume. Horizontal axis: timepoints 1, 2 and 3.
  A Spot 61 Plasminogen precursor
  B Spot 210 Igµ chaim C region
  C Spot 213 Igµ chaim C region
  D Spot 214 Igµ chaim C region
  E Spot 445 b2-glycoprotein I precursor
  F Spot 453 Complement C1R subcomponent precursor
  G Spot 461 b2 glycoprotein I precursor
  H Spot 466 b2-glycoprotein I precursor
  I Spot 553 Pigment epithelium-derived factor precursor
  J Spot 557 Pigment epithelium-derived factor precursor
  K Spot 559 Pigment epithelium-derived factor precursor
  L Spot 563 Pigment epithelium-derived factor precursor
  M Spot 570 Pigment epithelium-derived factor precursor
  N Spot 673
  O Spot 712 Transthyretin precursor
  P Spot 722 a1-microglobulin
  Q Spot 728 a1-microglobulin
  R Spot 730 a1-microglobulin
  S Spot 734 a1-microglobulin
  T Spot 735 a1-microglobulin
  U Spot 741 a1-microglobulin
  Spot 760 Complement factor H-related protein 2 precursor
  W Spot 771 Complement C3 precursor, a chain
  X Spot 781 Complement C3 precursor, a chain/Complement C4 precursor
  Y Spot 785 Complement factor D precursor
  Z Spot 760 Complement D precursor
  AA Spot 825 Plasma retinol-binding protein precursor
  BB Spot 826 Plasma retinol-binding protein precursor
  CC Spot 847 b2-glycoprotein precursor FIG. 7 Histograms of the time course of protein regulations from disease (dark grey) and control (light grey) samples of table 4 at timepoints 1, 2 and 3. Vertical axis: normalised spot volume. Horizontal axis: timepoints 1, 2 and 3.
  A Spot 56 Ceruloplasmin precursor (Ferroxidase)
  B Spot 113 Complement factor B precursor
  C Spot 149 a2-macroglobulin precursor
  D Spot 150 a2-macroglobulin precursor
  E Spot 238 Inter-a-trypsin inhibitor heavy chain H1 precursor
  F Spot 242 Inter-a-trypsin inhibitor heavy chain H1 precursor
  Spot 243 Inter-a-trypsin inhibitor heavy chain H1 precursor
  H Spot 463 Complement C1r subcomponent precursor
  I Spot 464 Complement C1r subcomponent precursor
  J Spot 498
  K Spot 510 Hemopexin precursor (b1B-glycoprotein)
  L Spot 515 Hemopexin precursor (b1B-glycoprotein)
  M Spot 551 Hemopexin precursor (b1B-glycoprotein)
  N Spot 562 Leucine-rich a2-glycoprotein precursor
  O Spot 622 Apolipoprotein A-IV precursor
  P Spot 657 Translation initiation factor 3 subunit 10/Ceruloplasmin precursor
  Q Spot 711 Complement C4-pre/Complemen C4-b pre
  R Spot 854 a1B-glycoprotein precursor FIG. 8 PCA scores plot of the control data set containing all gels.
Figure 6:
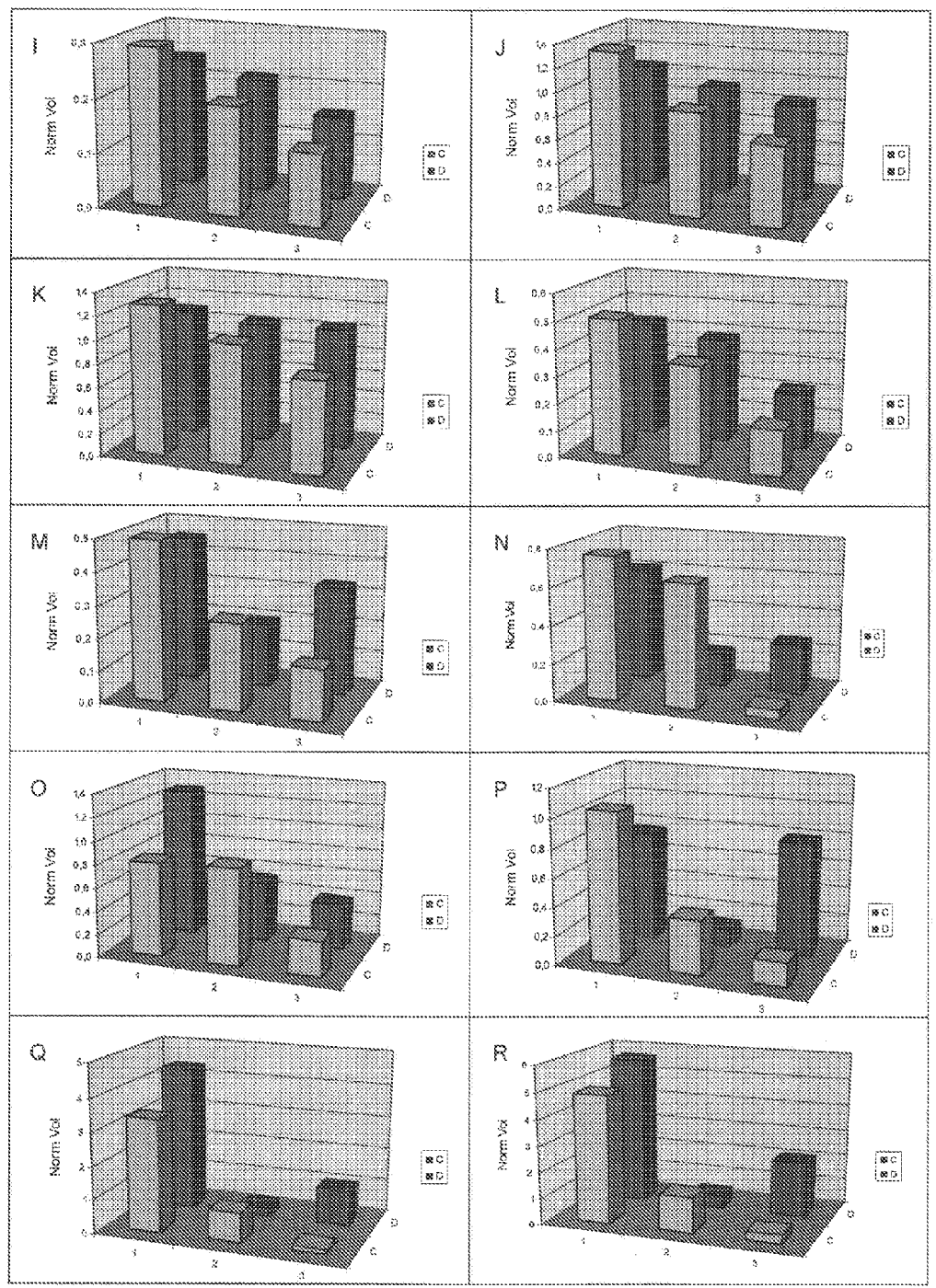
Figure 6:
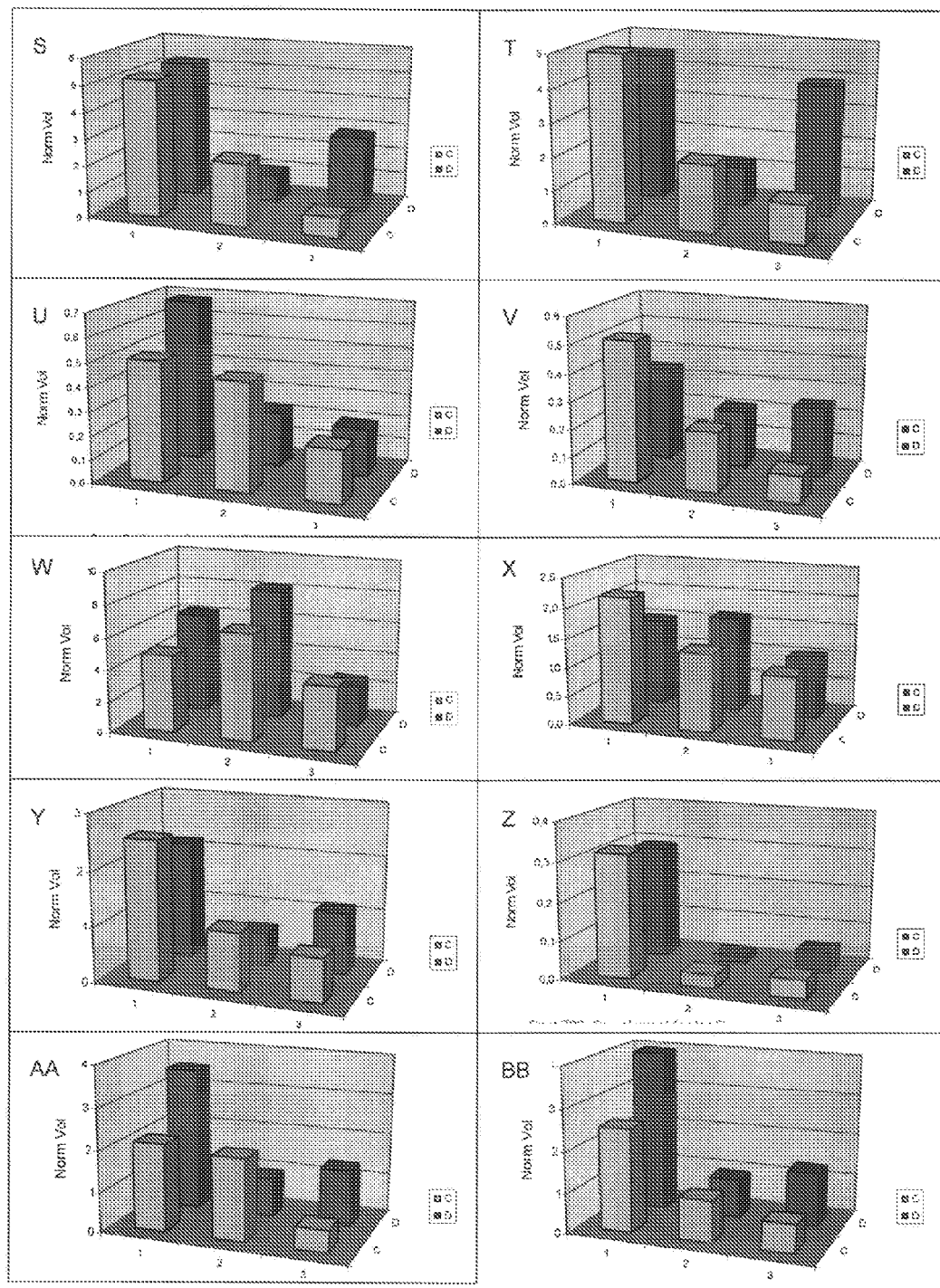
Figure 6:
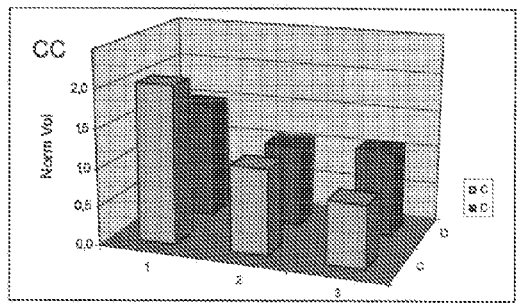
Figure 7:
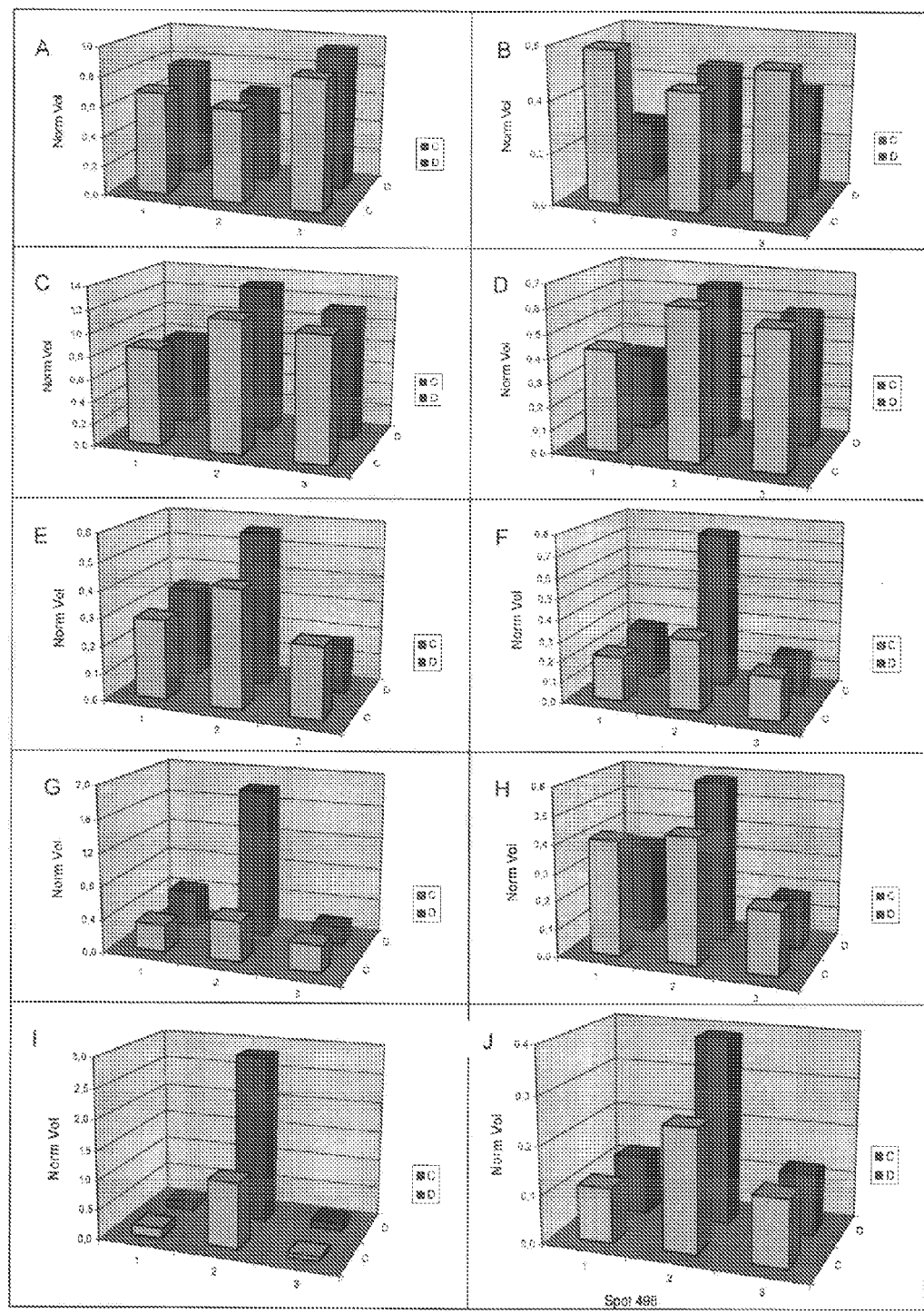
Figure 7:
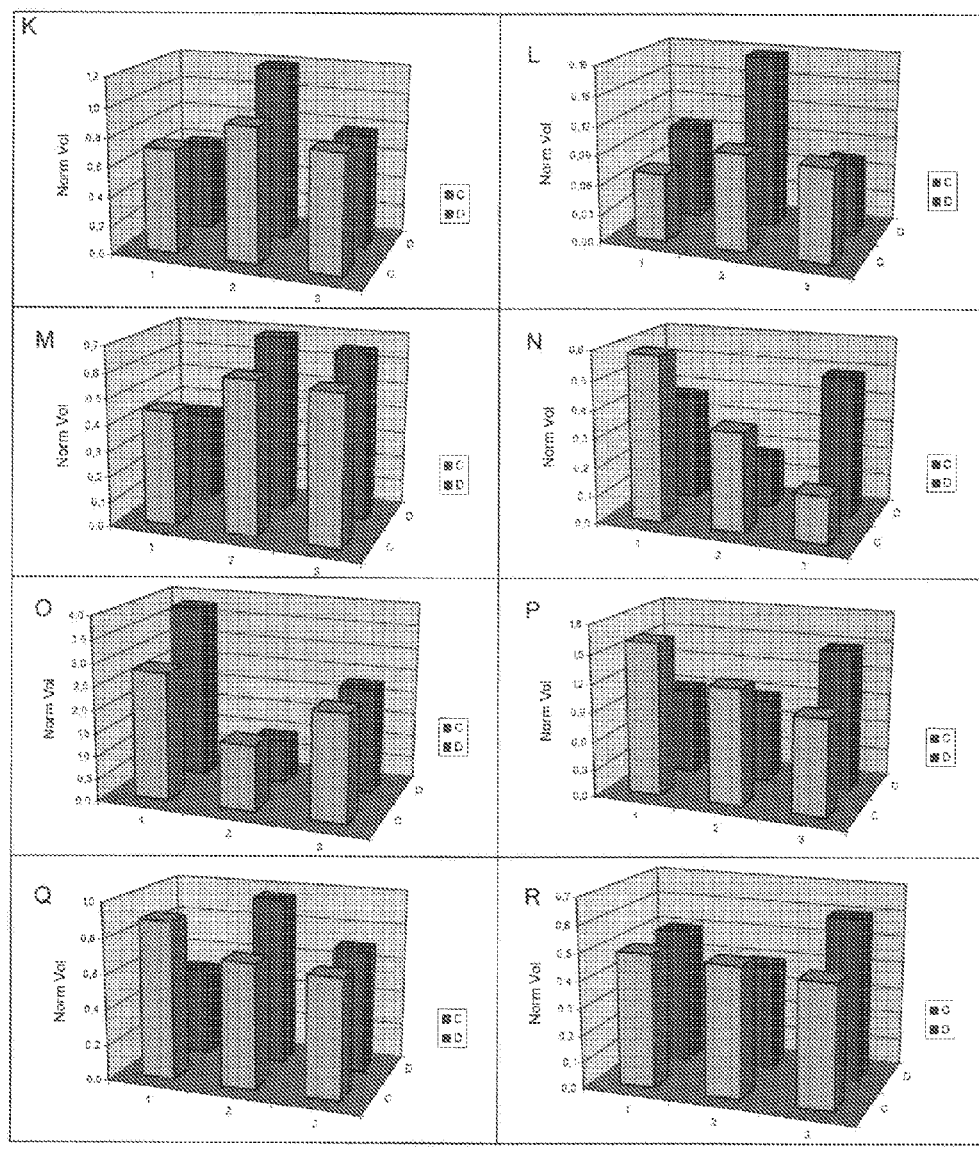

Renal damage may arise from, for example, transplant rejection, disease, toxicity and ischemic injury.

Renal transplant rejection is preferably chronic rejection, usually defined as rejection occurring six months or more after the transplant. Rejection may also be acute rejection, usually defined as rejection occurring up to six months after the transplant.

Disease may include Alport's Syndrome, Amyloidosis, Diabetes and the kidney, Fabry Disease, Focal and segmental Glomerulosclerosis (FSGS), Henoch-Schonlein purpura, Iga nephropathy (Berger's disease), Infantile Polycystic Disease, Kidney Stones, Haematuria Syndrome, Lupus and Lupus Kidney Disease, Membranoproliferative Glomerulonephritis (MPGN), Microscopic Polyarteris, Minimal Change Nepropathy, Reflux nephropathy, Renal artery stenosis, Vasculitis, Vesico-Ureteric Reflux and Wegeners granulomatosis Toxicity may be, for example, a side effect of drug treatment.

Marker Protein

The marker proteins disclosed herein may find use in diagnosis, prognosis or treatment in a variety of ways. The proteins themselves, or fragments thereof, may be detected in a diagnostic or prognostic assay as described below.

Marker proteins may be selected from any of the proteins shown in Table 4 or Table 5. Preferred marker proteins are N-acetylmuramoyl-L-alanine amidase precursor, adiponectin, AMBP protein precursor ($\alpha_1$-microglobulin), C4b-binding protein $\alpha$-chain precursor, ceruloplasmin precursor, complement C3 precursor, complement component C9 precursor, complement factor D precursor, $\alpha_{1B}$-glycoprotein, $\beta_2$-glycoprotein I precursor, heparin cofactor II precursor, Ig $\mu$ Chain C region protein, Leucine-rich $\alpha_2$-glycoprotein precursor, pigment epithelium-derived factor precursor, plasma retinol-binding protein precursor and translation initiation factor 3 subunit 10.

The term "marker protein" or "biomarker" includes all biologically relevant forms of the protein identified, including post-translationally modified forms. For example, the marker protein can be present in the body tissue in a glycosylated, phosphorylated, multimeric or precursor form.

Fragments of proteins to be detected or used for detection may be 10 or more, 20 or more, 30 or more, 40 or more, 60 or more, 70 or more, 80 or more, 100 or more, 150 or more, 200 or more, 250 or more, 300 or more, 350 or more, 400 or more or 500 or more amino acids in length.

Fragments of nucleic acids to be detected or used for detection may be 10 or more, 20 or more, 30 or more, 40 or more, 60 or more, 70 or more, 80 or more, 100 or more, 150 or more, 200 or more, 250 or more, 300 or more, 350 or more, 400 or more, 500 or more, 600 or more, 700 or more, 800 or more, 900 or more or 1000 or more basis in length.

Detection

A marker protein may have its expression modulated, i.e. quantitatively increased or decreased, in patients with renal damage. The degree to which expression differs in normal versus damage states need only be large enough to be visualised via standard characterisation techniques, such as silver staining of 2D-electrophoretic gels or immunological detection methods including Western blotting or radioimmunoassay. Other such standard characterisation techniques by which expression differences may be visualised are well known to those skilled in the art. These include successive chromatographic separations of fractions and comparisons of the peaks, capillary electrophoresis, separations using micro-channel networks, including on a micro-chip, and mass spectrometry methods including SELDI_TOF and MRM.

Chromatographic separations can be carried out by high performance liquid chromatography as described in Pharmacia literature, the chromatogram being obtained in the form of a plot of absorbance of light at 280 nm against time of separation. The material giving incompletely resolved peaks is then re-chromatographed and so on.

Capillary electrophoresis is a technique described in many publications, for example in the literature "Total CE Solutions" supplied by Beckman with their P/ACE 5000 system. The technique depends on a applying an electric potential across the sample contained in a small capillary tube. The tube has a charged surface, such as negatively charged silicate glass. Oppositely charged ions (in this instance, positive ions) are attracted to the surface and then migrate to the appropriate electrode of the same polarity as the surface (in this instance, the cathode). In this electroosmotic flow (EOF) of the sample, the positive ions move fastest, followed by uncharged material and negatively charged ions. Thus, proteins are separated essentially according to charge on them.

Micro-channel networks function somewhat like capillaries and can be formed by photoablation of a polymeric material. In this technique, a UV laser is used to generate high energy light pulses that are fired in bursts onto polymers having suitable UV absorption characteristics, for example polyethylene terephthalate or polycarbonate. The incident photons break chemical bonds with a confined space, leading to a rise in internal pressure, mini-explosions and ejection of the ablated material, leaving behind voids which form micro-channels. The micro-channel material achieves a separation based on EOF, as for capillary electrophoresis. It is adaptable to micro-chip form, each chip having its own sample injector, separation column and electrochemical detector: see J. S. Rossier et al., 1999, Electrophoresis 20: pages 727-731.

Other methods include performing a binding assay for the marker protein. Any reasonably specific binding agent can be used. Preferably the binding agent is labelled. Preferably the assay is an immunoassay, especially between the marker and an antibody that recognises the protein, especially a labelled antibody. It can be an antibody raised against part or all of the marker protein, for example a monoclonal antibody or a polyclonal anti-human antiserum of high specificity for the marker protein.

Where the binding assay is an immunoassay, it may be carried out by measuring the extent of the protein/antibody interaction. Any known method of immunoassay may be used. A sandwich assay is preferred. In an exemplary sandwich assay, a first antibody to the marker protein is bound to the solid phase such as a well of a plastics microtitre plate, and incubated with the sample and with a labelled second antibody specific for the protein to be assayed. Alternatively, an antibody capture assay can be used. Here, the test sample is allowed to bind to a solid phase, and the anti-marker protein antibody is then added and allowed to bind. After washing away unbound material, the amount of antibody bound to the solid phase is determined using a labelled second antibody, anti- to the first.

In another embodiment, a competition assay is performed between the sample and a labelled marker protein or a peptide derived therefrom, these two antigens being in competition for a limited amount of anti-marker protein antibody bound to a solid support. The labelled marker protein or peptide thereof can be pre-incubated with the antibody on the solid phase, whereby the marker protein in the sample displaces part of the marker protein or peptide thereof bound to the antibody.

In yet another embodiment, the two antigens are allowed to compete in a single co-incubation with the antibody. After removal of unbound antigen from the support by washing, the amount of label attached to the support is determined and the amount of protein in the sample is measured by reference to standard titration curves established previously.

The binding agent in the binding assay may be a labelled specific binding agent, which may be an antibody or other specific binding agent. The binding agent will usually be labelled itself, but alternatively it may be detected by a secondary reaction in which a signal is generated, e.g. from another labelled substance.

The label may be an enzyme. The substrate for the enzyme may be, for example, colour-forming, fluorescent or chemiluminescent.

An amplified form of assay may be used, whereby an enhanced "signal" is produced from a relatively low level of protein to be detected. One particular form of amplified immunoassay is enhanced chemiluminescent assay. Conveniently, the antibody is labelled with horseradish peroxidase, which participates in a chemiluminescent reaction with luminol, a peroxide substrate and a compound which enhances the intensity and duration of the emitted light, typically 4-iodophenol or 4-hydroxycinnamic acid.

Another form of amplified immunoassay is immuno-PCR. In this technique, the antibody is covalently linked to a molecule of arbitrary DNA comprising PCR primers, whereby the DNA with the antibody attached to it is amplified by the polymerase chain reaction. See E. R. Hendrickson et al., Nucleic Acids Research 23: 522-529 (1995). The signal is read out as before.

The time required for the assay may be reduced by use of a rapid microparticle-enhanced turbidimetric immunoassay such as the type embodied by M. Robers et al., "Development of a rapid microparticle-enhanced turbidimetric immunoassay for plasma fatty acid-binding protein, an early marker of acute myocardial infarction", Clin. Chem. 1998; 44:1564-1567.

The full automation of any immunoassay contemplated in a widely used clinical chemistry analyser such as the COBAS™ MIRA Plus system from Hoffmann-La Roche, described by M. Robers et al. supra, or the AxSYM™ system from Abbott Laboratories, should be possible and applied for routine clinical diagnosis of kidney damage including kidney transplant rejection.

Alternatively, the diagnostic sample can be subjected to two dimensional gel electrophoresis to yield a stained gel and the increased or decreased concentration of the protein detected by an increased or decreased intensity of a protein-containing spot on the stained gel, compared with a corresponding control or comparative gel. The invention includes such a method, independently of the marker protein identification given above.

In another method, the diagnostic sample can be subjected to Surface-Enhanced Laser Desorption Ionisation—Time of Flight mass spectrometry (SELDI-TOF). In this method the sample is typically a body fluid and is added to the surface of a SELDI-TOF ProteinChip prior to analysis in the SELDI-TOF mass spectrometer. General methods of SELDI-TOF analysis for human tissue samples are provided in international patent application WO 01/25791. The ProteinChip system consists of aluminium chips to which protein samples can be selectively bound on the surface chemistry of the chip (e.g. anionic, cationic, hydrophobic, hydrophilic etc). Bound proteins are then co-crystallised with a molar excess of small energy-absorbing molecules. The chip is then analysed by short intense pulses of N2 320 nm UV laser with protein separation and detection being by time of flight mass spectrometry. Spectral profiles of each group within an experiment are compared and any peaks of interest can be further analysed using techniques as described below to establish the identity of the protein.

The diagnostic sample can be subjected to analysis by multiple reaction monitoring (MRM) on an ion-trap mass spectrometer. Based on the mass spectrometry profiles of the marker proteins described below single tryptic peptides with specific known mass and amino acid sequences are identified that possess good ionising characteristics. The mass spectrometer is then programmed to specifically survey for peptides of the specific mass and sequence and report their relative signal intensity. Using MRM it is possible to survey for up to 5, 10, 15, 20, 25, 30, 40, 50 or 100 different marker proteins in a single LC-MS run. The intensities of the MRM peptides of the marker proteins in the diagnostic sample are compared with those found in samples from subjects without kidney damage and/or kidney transplant rejection allowing the diagnosis of kidney damage and/or kidney transplant rejection to be made.

The MRM assay can be made more truly quantitative by the use of internal reference standards consisting of synthetic absolute quantification (AQUA) peptides corresponding to the MRM peptide of the marker protein wherein one or more atoms have been substituted with a stable isotope such as carbon-14 or nitrogen-15 and wherein such substitutions cause the AQUA peptide to have a defined mass difference to the native MRM peptide derived from the diagnostic sample. By comparing the relative ion intensity of the native MRM and AQUA peptides the true concentration of the parent protein in the diagnostic sample can thus be determined. General methods of absolute quantitation are provided in Gerber, Scott A, et al. "Absolute quantification of proteins and phosphoproteins from cell lysates by tandem MS" PNAS, Jun. 10, 2003. Vol 100. No 12. p 6940-6945.

Alternatively, antibodies to marker proteins may be detected in a patient sample, using marker proteins or fragments thereof as a detection agent, for example in an ELISA. An altered concentration of marker proteins may be detected by detecting the presence or an altered amount of autoantibody thereto, compared with the level of autoantibody in a control sample. The level of autoantibody can be detected by Western blot (from 1D or 2D electrophoresis) against kidney tissue obtained from biopsy or surgical removal, or kidney-derived cell lines grown in vitro, or by enzyme-linked immunosorbent assay (ELISA), protein microarray or bead suspension array using purified proteins.

By way of example, detection of autoantibodies to proteins differentially increased in kidney damage and/or kidney rejection patients can be carried out as follows. Recombinant proteins are expressed in baculovirus infected insect cells and used to coat the surface of microtitre plates. A sample from patients suspected of having kidney damage and/or kidney rejection is added to duplicate wells of each microtitre plate and incubated at 37° C. for 1 hour. Plates are aspirated and washed prior to the addition of a horse-radish peroxidase (HRP) labelled anti-human IgG antiserum and incubated for 1 hour at 37° C. Finally, binding of the antihuman antiserum is revealed by aspirating the plates, washing, and then adding tetra-methylbenzidine (TMB) which in the presence of HRP produces a coloured product the intensity of which is measured by reading the plates at 450 nm. An identical set of plates is tested with the exception that the second antibody is a HRP labelled anti-human IgM antiserum. The levels of IgG and/or IgM autoantibodies to each of the kidney damage and/or kidney rejection marker proteins is altered when compared to the levels found in samples from healthy individuals.

It is contemplated within the invention to use (i) an antibody chip or array of chips, or a bead suspension array capable of detecting one or more proteins that interact with that antibody; or (ii) a protein chip or array of chips, or bead suspension array capable of detecting one or more autoantibodies that interact with the marker proteins; or (iii) a combination of both antibody arrays and protein arrays.

An "antibody array" or "antibody microarray" is an array of unique addressable elements on a continuous solid surface whereby at each unique addressable element an antibody with defined specificity for an antigen is immobilised in a manner allowing its subsequent capture of the target antigen and subsequent detection of the extent of such binding. Each unique addressable element is spaced from all other unique addressable elements on the solid surface so that the binding and detection of specific antigens does not interfere with any adjacent such unique addressable element.

A "bead suspension array" is an aqueous suspension of one or more identifiably distinct particles whereby each particle contains coding features relating to its size and colour or fluorescent signature and to which all of the beads of a particular combination of such coding features is coated with an antibody with a defined specificity for an antigen in a manner allowing its subsequent capture of the target antigen and subsequent detection of the extent of such binding. Examples of such arrays can be found at www.luminexcorp.com where application of the xMAP® bead suspension array on the Luminex® 100™ System is described.

Alternatively, differential expression of nucleic acids encoding marker proteins may be used as a detection method.

Expression of nucleic acid may be detected by methods known in the art, such as RT-PCR, Northern blotting or in situ hybridisation such as FISH.

The diagnosis can be based on the differential expression of one, two, three or more of the marker proteins, or of one, two, three or more autoantibodies raised against such proteins, or a combination of both. Further, it can be part of a wider diagnosis in which two or more different diseases are diagnosed. Renal damage and kidney transplant rejection can be diagnosed together with at least one other disease, which may or may not be a renal disease, in the same sample of body tissue, by a method which includes detecting a change in concentration of another protein in the diagnostic sample, compared with a sample of a control, normal human subject. These other disease(s) can be any which are diagnosable in a body tissue.

Diagnosis and Prognosis

The term "diagnosis", as used herein, includes the provision of any information concerning the existence, non-existence or probability of renal damage, disease or renal transplant rejection in a patient. It further includes the provision of information concerning the type or classification of the disorder or of symptoms which are or may be experienced in connection with it. It encompasses prognosis of the medical course of the condition.

The methods described herein are useful for both the diagnosis and/or prognosis of renal damage, including chronic renal transplant rejection. Renal damage or rejection may be indicated if one or more markers is present at increased or decreased concentration. For some markers, both an increased or a decreased concentration may be indicative of damage or rejection.

The invention can be used to determine the stage of progression of kidney damage including kidney transplant rejection, if desired, with reference to results obtained earlier from the same patient or by reference to standard values that are considered typical of the stage of the disease. In this way, the invention can be used to determine whether, for example after treatment of the patient with a drug or candidate drug, the disease has progressed or not. The result can lead to a prognosis of the outcome of the disease.

The methods typically employ a biological sample from patient such as blood, serum, tissue, plasma, urine or other suitable body fluids. A preferred patient sample is blood or blood products such as serum or plasma. Plasma or other sample fluids may be depleted of high abundance proteins prior to testing, as described below. Alternatively, the diagnostic sample may be a tissue section which is fixed, e.g. by freezing or embedding in paraffin.

The diagnostic methods and uses of the invention may comprise the steps of (i) detecting marker protein, nucleic acid or antibody expression in a test sample or samples, (ii) detecting marker protein, nucleic acid or antibody expression in a control sample or samples, and (iii) comparing the level of expression on the control and test samples to establish whether the marker is differentially expressed in the test sample. Alternatively, a pre-existing control may be used for comparison. Preferably, the control sample is from the same tissue or body fluid type as the test sample.

In general, the term "control" refers to a normal human subject, i.e. one not suffering from renal damage, or to healthy tissue of the same human subject as the diagnostic sample. In some cases, particularly when the stages of renal transplant rejection are being monitored progressively, or when a course of treatment is being monitored, a comparison may instead be made with the concentration previously seen in the same subject at an earlier stage of progression of the disease, or at an earlier time point.

The step of comparing with a control sample may not always be necessary, since in many cases it will be obvious to the skilled practitioner that the concentration is abnormally high or low.

"Differential expression", as used above, refers to at least one recognisable difference in protein or nucleic acid expression. It may be a quantitatively measurable, semi-quantitatively estimatable or qualitatively detectable difference in tissue or body fluid p expression. Thus, a differentially expressed protein or nucleic acid may be strongly expressed in tissue or body fluid in the normal state and less strongly expressed or not expressed at all in the damaged state. Conversely, it may be strongly expressed in tissue or body fluid in the damage state and less strongly expressed or not expressed at all in the normal state. Further, expression may be regarded as differential if the protein or nucleic acid undergoes any recognisable change between the two states under comparison.

Samples may be taken daily, weekly, monthly or bimonthly after transplant. Daily or weekly samples may be appropriate for detection of acute rejection, while monthly or bimonthly samples are more appropriate for detection of chromic rejection.

Treatment

It will be understood that where treatment is concerned, treatment includes any measure taken by the physician to alleviate the effect of renal damage or transplant rejection on a patient. Thus, although reversal of the damage or elimination of the damage or effects of rejection is a desirable goal, effective treatment will also include any measures capable of achieving reduction in the degree of damage or severity of the effects.

In one aspect, the invention provides a method of treatment by the use of an agent that will restore the expression of one or more differentially expressed proteins in the kidney damage and/or kidney transplant rejection state towards that found in the normal state in order to prevent the development or progression of kidney damage and/or organ transplant rejection. Preferably, the expression of the protein is restored to that of the normal state.

In a further aspect, the present invention provides a method whereby the pattern of differentially expressed proteins in a sample from an individual with kidney damage and/or kidney transplant rejection is used to predict the most appropriate and effective therapy to alleviate the kidney damage and/or kidney transplant rejection Assay Methods Also provided is a method of screening an agent to determine its usefulness in treating a kidney damage and/or kidney transplant rejection, the method comprising:
(a) obtaining a sample of from, or representative of, a subject having kidney damage and/or kidney transplant rejection symptoms, who or which has been treated with the agent being screened;
(b) determining the presence, absence or degree of expression of a marker protein or proteins as disclosed herein in the sample from, or representative of, the treated subject; and,
(c) selecting or rejecting the agent according to the extent to which it changes the expression, activity or amount of the marker protein or proteins in the treated subject having kidney damage and/or kidney transplant rejection symptoms.

Preferably, the agent is selected if it converts the expression of the differentially expressed protein towards that of a normal subject. More preferably, the agent is selected if it converts the expression of the protein or proteins to that of the normal subject.

Also provided is a method of screening an agent to determine its usefulness in treating kidney damage and/or kidney transplant rejection, the method comprising:
(a) obtaining over time samples from, or representative of, a subject having kidney damage and/or kidney transplant rejection symptoms, who or which has been treated with the agent being screened;
(b) determining the presence, absence or degree of expression of a marker protein or proteins as disclosed herein in said samples; and,
(c) determining whether the agent affects the change over time in the expression of the marker protein in the treated subject having kidney damage and/or kidney transplant rejection symptoms.

Samples taken over time may be taken at intervals of weeks, months or years. For example, samples may be taken at monthly, two-monthly, three-monthly, four-monthly, six-monthly, eight-monthly or twelve-monthly intervals.

A change in expression over time may be an increase or decrease in expression, compared to the initial level of expression in samples from the subject and/or compared to the level of expression in samples from normal subjects. The agent is selected if it slows or stops the change of expression over time.

In the screening methods described above, subjects having differential levels of protein expression comprise:
(a) normal subjects and subjects having kidney damage and/or kidney transplant rejection symptoms; and,
(b) subjects having kidney damage and/or kidney transplant rejection symptoms which have not been treated with the agent and subjects having kidney damage and/or kidney transplant rejection symptoms which have been treated with the agent.

Compositions

The markers or antibodies thereto described herein may be formulated into compositions, in particular therapeutic compositions. The preparation of therapeutic compositions which contain polypeptides or proteins as active ingredients is well understood in the art. Therapeutic compositions may be liquid solutions or suspensions, solid forms suitable for solution in, or suspension in a liquid prior to ingestion may also be prepared. The therapeutic may also be emulsified. The active therapeutic ingredient is typically mixed with inorganic and/or organic carriers which are pharmaceutically acceptable and compatible with the active ingredient. The carriers are typically physiologically acceptable excipients comprising more or less inert substances when added to the therapeutic composition to confer suitable consistencies and form to the composition. Suitable carriers are for example, water, saline, dextrose, glycerol, and the like and combinations thereof. In addition, if desired the composition can contain minor amounts of auxiliary substances such as wetting or emulsifying agents and pH buffering agents which enhance the effectiveness of the active ingredient. Therapeutic compositions containing carriers that have nutritional value are also contemplated.

A composition may be administered alone or in combination with other treatments, either simultaneously or sequentially dependent upon the condition to be treated.

Liquid pharmaceutically administrable compositions can, for example, be prepared by dissolving, dispersing, etc, a fusion protein of the invention optional pharmaceutical adjuvants in a carrier, such as, for example, water, saline aqueous dextrose, glycerol, ethanol, and the like, to thereby form a solution or suspension. If desired, the composition to be administered may also auxiliary substances such as pH buffering agents and the like. Actual methods of preparing such dosage forms are known, or will be apparent, to those skilled in this art; for example, see Remington's Pharmaceutical Sciences, 20th Edition, 2000, pub. Lippincott, Williams & Wilkins.

Administration

The pharmaceutical compositions of the present invention may be administered in a number of ways depending upon whether local or systemic treatment is desired and upon the area to be treated. Administration may be topical (including ophthalmic, vaginal, rectal, intranasal, epidermal and transdermal), oral or parenteral. Parenteral administration includes intravenous drip, subcutaneous, intraperitoneal or intramuscular injection, pulmonary administration, e.g., by inhalation or insufflation, or intracranial, e.g., intrathecal or intraventricular, administration. For oral administration, it has been found that oligonucleotides with at least one 2'-substituted ribonucleotide are particularly useful because of their absorption and distribution characteristics. U.S. Pat. No. 5,591,721 issued to Agrawal et al. Oligonucleotides with at least one 2'-O-methoxyethyl modification are believed to be particularly useful for oral administration.

Where a composition as described herein is to be administered to an individual, administration is preferably in a "prophylactically effective amount" or a "therapeutically effective amount" (as the case may be, although prophylaxis may be considered therapy), this being sufficient to show benefit to the individual.

Administration may be, for example, daily, weekly or monthly. The actual amount administered, and rate and time-course of administration, will depend on the nature and severity of what is being treated. It will also depend upon toxicity of the therapeutic agent, as determined by pre-clinical and clinical trials. Prescription of treatment, e.g. decisions on dosage etc, is within the responsibility of general practitioners and other medical doctors.

Dosing

Dosing is dependent on severity and responsiveness of the condition to be treated, with course of treatment lasting from several days to several months or until a reduction in viral titre (routinely measured by Western blot, ELISA, RT-PCR, or RNA (Northern) blot, for example) is effected or a diminution of disease state is achieved. Optimal dosing schedules are easily calculated from measurements of drug accumulation in the body. Persons of ordinary skill can easily determine optimum dosages, dosing methodologies and repetition rates. Therapeutically or prophylactically effective amounts (dosages) may vary depending on the relative potency of individual compositions, and can generally be routinely calculated based on molecular weight and EC50s in in vitro and/or animal studies. For example, given the molecular weight of drug compound (derived from oligonucleotide sequence and chemical structure) and an experimentally derived effective dose such as an IC.sub.50, for example, a dose in mg/kg is routinely calculated. In general, dosage is from 0.001 .mu.g to 100 g and may be administered once or several times daily, weekly, monthly or yearly, or even every 2 to 20 years.

Nucleic Acids

Nucleic acid may of course be double- or single-stranded, cDNA or genomic DNA, or RNA. The nucleic acid may be wholly or partially synthetic, depending on design. Naturally, the skilled person will understand that where the nucleic acid according to the invention includes RNA, reference to the sequence shown should be construed as reference to the RNA equivalent, with U substituted for T. The present invention also encompasses the expression product of any of the nucleic acid sequences disclosed and methods of making the expression product by expression from encoding nucleic acid therefore under suitable conditions in suitable host cells.

Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Ausubel et al. eds., Wiley, 1994, and in summary in *Short Protocols in Molecular Biology*, Fifth Edition, Ausubel et al. eds., Current Protocols, 2002.

Antibodies

Antibodies against the marker proteins disclosed herein can be produced using known methods. These methods of producing antibodies include immunising a mammal (e.g. mouse, rat, rabbit, horse, goat, sheep or monkey) with the protein. Antibodies may be obtained from immunised animals using any of a variety of techniques known in the art, and screened, preferably using binding of antibody to antigen of interest. Isolation of antibodies and/or antibody-producing cells from an animal may be accompanied by a step of sacrificing the animal.

As an alternative or supplement to immunising a mammal with a protein, an antibody specific for the protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with the protein, or may be one constructed using sequences obtained from an organism which has been exposed to the antigen of interest.

The antibodies may bind or be raised against any biologically relevant state of the protein. Thus, for example, they can be raised against the unglycosylated form of a protein which exists in the body in a glycosylated form, against a more mature form of a precursor protein, e.g. minus its signal sequence, or against a peptide carrying a relevant epitope of the marker protein.

Antibodies may be polyclonal or monoclonal, and may be multispecific (including bispecific), chimeric or humanised antibodies. Antibodies according to the present invention may be modified in a number of ways. Indeed the term "antibody" should be construed as covering any binding substance having a binding domain with the required specificity. Thus, the invention covers antibody fragments, derivatives, functional equivalents and homologues of antibodies, including synthetic molecules and molecules whose shape mimics that of an antibody enabling it to bind an antigen or epitope.

Examples of antibody fragments, capable of binding an antigen or other binding partner, are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')$_2$ fragments, a bivalent fragment including two Fab fragments linked by a disulphide bridge at the hinge region. Single chain Fv fragments are also included.

Antibody fragments, which recognise specific epitopes, may be generated by known techniques. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternative, Fab expression libraries may be constructed (Huse, et al., 1989, Science 246: 1275-1281) to allow rapid and easy identification of monoclonal Fab fragments with the desired specificity.

The term "monoclonal antibody" as used herein refers to an antibody obtained from a substantially homogenous population of antibodies, i.e. the individual antibodies comprising the population are identical apart from possible naturally occurring mutations that may be present in minor amounts. Monoclonal antibodies can be produced by the method first described by Kohler and Milstein, Nature, 256:495, 1975 or may be made by recombinant methods, see Cabilly et al, U.S. Pat. No. 4,816,567, or Mage and Lamoyi in Monoclonal Antibody Production Techniques and Applications, pages 79-97, Marcel Dekker Inc, New York, 1987.

In the hybridoma method, a mouse or other appropriate host animal is immunised with the antigen by subcutaneous, intraperitoneal, or intramuscular routes to elicit lymphocytes that produce or are capable of producing antibodies that will specifically bind to the nanoparticles used for immunisation. Alternatively, lymphocytes may be immunised in vitro. Lymphocytes then are fused with myeloma cells using a suitable fusing agent, such as polyethylene glycol, to form a hybridoma cell, see Goding, Monoclonal Antibodies: Principles and Practice, pp. 59-103 (Academic Press, 1986).

The hybridoma cells thus prepared can be seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody producing cells, and are sensitive to a medium such as HAT medium.

Culture medium in which hybridoma cells are growing is assayed for production of monoclonal antibodies directed against the protein. Preferably, the binding specificity is determined by enzyme-linked immunoabsorbance assay (ELISA). The monoclonal antibodies of the invention are those that specifically bind to the protein.

In a preferred embodiment of the invention, the monoclonal antibody will have an affinity which is greater than micromolar or greater affinity (i.e. an affinity greater than $10^{-6}$ mol) as determined, for example, by Scatchard analysis, see Munson & Pollard, Anal. Biochem., 107:220, 1980.

After hybridoma cells are identified that produce neutralising antibodies of the desired specificity and affinity, the clones can be subcloned by limiting dilution procedures and grown by standard methods. Suitable culture media for this purpose include Dulbecco's Modified Eagle's Medium or RPM1-1640 medium. In addition, the hybridoma cells may be grown in vivo as ascites tumours in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Nucleic acid encoding the monoclonal antibodies of the invention is readily isolated and sequenced using procedures well known in the art, e.g. by using oligonucleotide probes that are capable of binding specifically to genes encoding the heavy and light chains of murine antibodies. The hybridoma cells of the invention are a preferred source of nucleic acid encoding the antibodies or fragments thereof. Once isolated, the nucleic acid is ligated into expression or cloning vectors, which are then transfected into host cells, which can be cultured so that the monoclonal antibodies are produced in the recombinant host cell culture.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies, humanised antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2 188 638 A or EP 0 239 400 A. Cloning and expression of chimeric antibodies are described in EP 0 120 694 A and EP 0 125 023 A.

An antibody against a marker protein described herein will bind to said protein. Preferably, said antibody specifically binds said protein. By "specific" is meant that the antibody binds to said protein with an affinity significantly higher than it displays for other molecules.

The invention will now be described in more detail with reference to the following examples, which are provided for illustrative purposes only, and are not intended to limit the scope of the invention.

All patent and literature references cited herein are hereby incorporated by reference in their entirety.

EXPERIMENTAL

In order to discover novel biomarker candidates for renal allograft rejection, 240 serum samples of kidney transplant recipients from the Oxford Transplant Centre were analyzed by expression proteomics. These high-quality serum samples were depleted of six high-abundant proteins and analyzed by 2D-electrophoresis. Image analysis and peptide mass fingerprinting (PMF) of one half of the serum samples resulted in a set of 29 regulated proteins 20 of which are related to immune and inflammatory response as well as other processes during renal rejection or renal disease. The remaining 9 proteins have not been described in the context of renal rejection or renal disease so far. A group of 16 proteins of the total number of 29 regulated proteins may serve as independent indicators for renal allograft rejection. These findings were confirmed by a validation study run with the second half of the serum samples.

Methods

Renal Rejection Serum Samples 240 serum samples were received from the Oxford Transplant Centre. 120 disease serum samples came from 40 kidney transplant recipients with biopsy proven chronic allograft nephropathy CAN and another 120 control serum samples came from 40 recipients with a functioning graft without evidence of CAN, three different points in time each. Classification of samples is shown in table 1 and 2.

TABLE 1

Classification of renal rejection disease serum samples.

| Point in time | Description | Disease samples # |
|---|---|---|
| Time 1 | Pre-transplant, close to the time of transplant. | 1-1 to 40-1 |
| Time 2 | Before the development of CAN, but at a time when potential mediators of the process may be circulating (generally at 1 year post transplant). If CAN was diagnosed at 1 year, then serum selected at a suitable time point within the first year. | 1-2 to 40-2 |
| Time 3 | As near as possible to the time of biopsy diagnosis of CAN | 1-3 to 40-3 |

TABLE 2

Classification of renal rejection control serum samples.

| Point in time | Description | Control samples # |
|---|---|---|
| Time 1 | Pre-transplant, close to the time of transplant. | 41-1 to 80-1 |
| Time 2 | Approximately 1 year post transplant | 41-2 to 80-2 |
| Time 3 | Approximately 3 years post transplant | 41-3 to 80-3 |

Samples were divided into two groups: study group and validation group. Each group contained samples from 20 disease patients and 20 control patients (three different points in time each) which were randomly chosen. For classification of samples see table 3A and 3B.

TABLE 3A

Classification of renal rejection serum samples for study group.

| Disease-1 | | Disease-2 | | Disease-3 | | Control-1 | | Control-2 | | Control-3 | |
|---|---|---|---|---|---|---|---|---|---|---|---|
| 1 | −1 | 1 | −2 | 1 | −3 | 41 | −1 | 41 | −2 | 41 | −3 |
| 5 | −1 | 5 | −2 | 5 | −3 | 42 | −1 | 42 | −2 | 42 | −3 |
| 8 | −1 | 8 | −2 | 8 | −3 | 45 | −1 | 45 | −2 | 45 | −3 |
| 12 | −1 | 12 | −2 | 12 | −3 | 47 | −1 | 47 | −2 | 47 | −3 |
| 15 | −1 | 15 | −2 | 15 | −3 | 50 | −1 | 50 | −2 | 50 | −3 |
| 16 | −1 | 16 | −2 | 16 | −3 | 51 | −1 | 51 | −2 | 51 | −3 |
| 17 | −1 | 17 | −2 | 17 | −3 | 53 | −1 | 53 | −2 | 53 | −3 |
| 18 | −1 | 18 | −2 | 18 | −3 | 54 | −1 | 54 | −2 | 54 | −3 |
| 19 | −1 | 19 | −2 | 19 | −3 | 58 | −1 | 58 | −2 | 58 | −3 |
| 20 | −1 | 20 | −2 | 20 | −3 | 59 | −1 | 59 | −2 | 59 | −3 |
| 21 | −1 | 21 | −2 | 21 | −3 | 64 | −1 | 64 | −2 | 64 | −3 |
| 22 | −1 | 22 | −2 | 22 | −3 | 65 | −1 | 65 | −2 | 65 | −3 |
| 23 | −1 | 23 | −2 | 23 | −3 | 68 | −1 | 68 | −2 | 68 | −3 |
| 24 | −1 | 24 | −2 | 24 | −3 | 69 | −1 | 69 | −2 | 69 | −3 |
| 26 | −1 | 26 | −2 | 26 | −3 | 70 | −1 | 70 | −2 | 70 | −3 |
| 28 | −1 | 28 | −2 | 28 | −3 | 71 | −1 | 71 | −2 | 71 | −3 |
| 29 | −1 | 29 | −2 | 29 | −3 | 76 | −1 | 76 | −2 | 76 | −3 |
| 30 | −1 | 30 | −2 | 30 | −3 | 78 | −1 | 78 | −2 | 78 | −3 |
| 35 | −1 | 35 | −2 | 35 | −3 | 79 | −1 | 79 | −2 | 79 | −3 |
| 39 | −1 | 39 | −2 | 39 | −3 | 80 | −1 | 80 | −2 | 80 | −3 |

TABLE 3B

Classification of renal rejection serum samples for validation group.

| Disease-1 | | Disease-2 | | Disease-3 | | Control-1 | | Control-2 | | Control-3 | |
|---|---|---|---|---|---|---|---|---|---|---|---|
| 2 | −1 | 2 | −2 | 2 | −3 | 43 | −1 | 43 | −2 | 43 | −3 |
| 3 | −1 | 3 | −2 | 3 | −3 | 44 | −1 | 44 | −2 | 44 | −3 |
| 4 | −1 | 4 | −2 | 4 | −3 | 46 | −1 | 46 | −2 | 46 | −3 |
| 6 | −1 | 6 | −2 | 6 | −3 | 48 | −1 | 48 | −2 | 48 | −3 |
| 7 | −1 | 7 | −2 | 7 | −3 | 49 | −1 | 49 | −2 | 49 | −3 |
| 9 | −1 | 9 | −2 | 9 | −3 | 52 | −1 | 52 | −2 | 52 | −3 |
| 10 | −1 | 10 | −2 | 10 | −3 | 55 | −1 | 55 | −2 | 55 | −3 |
| 11 | −1 | 11 | −2 | 11 | −3 | 56 | −1 | 56 | −2 | 56 | −3 |
| 13 | −1 | 13 | −2 | 13 | −3 | 57 | −1 | 57 | −2 | 57 | −3 |
| 14 | −1 | 14 | −2 | 14 | −3 | 60 | −1 | 60 | −2 | 60 | −3 |
| 25 | −1 | 25 | −2 | 25 | −3 | 61 | −1 | 61 | −2 | 61 | −3 |
| 27 | −1 | 27 | −2 | 27 | −3 | 62 | −1 | 62 | −2 | 62 | −3 |
| 31 | −1 | 31 | −2 | 31 | −3 | 63 | −1 | 63 | −2 | 63 | −3 |
| 32 | −1 | 32 | −2 | 32 | −3 | 66 | −1 | 66 | −2 | 66 | −3 |
| 33 | −1 | 33 | −2 | 33 | −3 | 67 | −1 | 67 | −2 | 67 | −3 |
| 34 | −1 | 34 | −2 | 34 | −3 | 72 | −1 | 72 | −2 | 72 | −3 |
| 36 | −1 | 36 | −2 | 36 | −3 | 73 | −1 | 73 | −2 | 73 | −3 |
| 37 | −1 | 37 | −2 | 37 | −3 | 74 | −1 | 74 | −2 | 74 | −3 |
| 38 | −1 | 38 | −2 | 38 | −3 | 75 | −1 | 75 | −2 | 75 | −3 |
| 40 | −1 | 40 | −2 | 40 | −3 | 77 | −1 | 77 | −2 | 77 | −3 |

Study Design

Two types of image analysis were performed: (1) time course study of control and disease patients and (2) control vs. disease patients. 2D-gels of samples of the study group were compared as follows:

disease-1 vs. disease-3, control-1 vs. control-3, disease-1 vs. control-1, disease-3 vs. control-3 disease-1 vs. disease-2, disease-2 vs. disease-3, control-1 vs. control-2, control-2 vs. control-3.

Again, numbers 1, 2 and 3 refer to the three different points in time samples were taken. Then the outcome of analytical 2D-gels of the validation group was compared with that of the study group to validate regulated protein spots and potential biomarker candidates of the study group. For preparative 2D-gels, 6 to 7 serum samples of disease and control samples of the study and the validation group were pooled, respectively.

Proteomics Procedure

The proteomics procedure was done according to standard procedures of Proteome Sciences R&D. In brief, 240 renal rejection serum samples were depleted of 6 high-abundant proteins by means of the MARS (Multiple Affinity Removal System) column (Agilent). Depleted serum samples (100 µg) were analyzed by analytical 2-DE (pH 3-10NL, 10% SDS-PAGE). Silver-stained analytical 2D-gels were quantitatively analyzed by Progenesis software (v2005) including spot detection, matching, background subtraction and normalization. After detection and matching of protein spots, the spot data was exported to MS Excel and a macro developed in-house was used to calculate the coefficient of variation (CV %), Mann-Whitney Test and regulation factor. Regulated spots were identified by the following selection criteria: spots have to be found in at least 60% of all gels of a group, up/down regulation at least 1.5-fold or at most 0.667-fold and significance value $p<0.005$. In order to identify the corresponding proteins, regulated spots were picked from preparative, CBB-stained 2D-gels of depleted disease and control samples (350 µg, 6 to 7 individual samples each) and trypsinated by means of a Spot Handling Workstation (GE Healthcare). Resulting peptides were analyzed by MALDI-MS. The proteins were identified by comparing the obtained MALDI-MS-spectra with in-silico digests of proteins from databases (PMF Peptide Mass Fingerprinting).

Results

Identification of Regulated Proteins

Identification of regulated protein spots is shown in table 4 and table 5. Histograms of the time course of protein regulations from disease and control samples of point in time 1, 2 and 3 are listed in supplement B.

TABLE 4

Identification of regulated protein spots in study group/validation group.

| Spot no | Protein name | Swiss-Prot Acc. No. | EMBL Acc No | Expression ratio or trend of regulation in comparison | | | |
|---|---|---|---|---|---|---|---|
| | | | | C1 vs. C3 | D1 vs. D3 | C1 vs. D1 | C3 vs. D3 |
| 61 | Plasminogen precursor | P00747 | | 1.76/1.14 | + | + | − |
| 210 | Ig µ chain C region | P01871 | X17115 | 3.72/2.32 | + | − | − |
| 213 | Ig µ chain C region | P01871 | X17115 | 3.75/2.35 | + | + | − |
| 214 | Ig µ chain C region | P01871 | X17115 | 3.12/2.01 | + | − | − |
| 246 | C4b-binding protein alpha chain precursor | M31452; BC022312 | M31452; BC022312 | + | + | + | 1.86/0.84 |
| 272 | Heparin cofactor II precursor | P05546 | M12849; X03498 | + | − | 1.52/0.81 | + |

TABLE 4-continued

Identification of regulated protein spots in study group/validation group.

| Spot no | Protein name | Swiss-Prot Acc. No. | EMBL Acc No | Expression ratio or trend of regulation in comparison | | | |
|---|---|---|---|---|---|---|---|
| | | | | C1 vs. C3 | D1 vs. D3 | C1 vs. D1 | C3 vs. D3 |
| 286 | N-acetylmuramoyl-L-alanine amidase precursor | Q96PD5 | AF384856 | + | − | 2.17/0.86 | + |
| 291 | Complement component C9 precursor, chain a or b | P02748 | BC020721; K02766 | + | − | 1.51/1.50 | + |
| 445 | $\beta_2$-glycoprotein I precursor (Apolipoprotein H) | P02749 | X58100; X53595; X57847; M62839; S80305; BC020703; BC026283 | 0.46/0.53 | + | − | + |
| 453 | Complement C1R subcomponent precursor, heavy chain | P00736 | | 0.41/0.65 | − | − | − |
| 461 | $\beta_2$-glycoprotein I precursor (Apolipoprotein H) | P02749 | See above | 0.22/0.40 | − | − | + |
| 466 | $\beta_2$-glycoprotein I precursor (Apolipoprotein H) | P02749 | See above | 0.42/0.59 | + | − | + |
| 553 | Pigment epithelium-derived factor precursor | P36955 | M76979; AF400442 | 0.45/0.96 | − | − | + |
| 555 | Leucine-rich $\alpha_2$-glycoprotein precursor | P02750 | AF403428; BC034389; BC070198 | − | + | − | 4.39/1.40 |
| 557 | Pigment epithelium-derived factor precursor | P36955 | See above | 0.51/0.98 | − | − | + |
| 559 | Pigment epithelium-derived factor precursor | P36955 | See above | 0.62/0.96 | − | − | + |
| 563 | Pigment epithelium-derived factor precursor | P36955 | See above | 0.33/0.55 | − | − | + |
| 570 | Pigment epithelium-derived factor precursor | P36955 | See above | 0.32/0.69 | − | − | 2.11/0.91 |
| 591 | Complement C3 precursor | P01024 | K02765 | − | + | 0.43/0.57 | + |
| 712 | Transthyretin precursor, syn: Prealbumin | P02766 | | 0.37/0.64 | 0.31/0.27 | + | + |
| 722 | AMBP protein precursor contains: alpha-1-microglobulin | P02760 | X04225 | 0.16/0.16 | + | − | 4.92/2.89 |
| 728 | AMBP protein precursor ($\alpha_1$-microglobulin) | P02760 | X04225 | 0.04/0.04 | 0.24/0.32 | + | 7.72/9.79 |
| 730 | AMBP protein precursor ($\alpha_1$-microglobulin) | P02760 | X04225 | 0.07/0.64 | 0.37/0.21 | + | 6.55/4.36 |
| 734 | AMBP protein precursor ($\alpha_1$-microglobulin) | P02760 | X04225 | 0.14/0.16 | 0.54/0.33 | + | 3.82/2.02 |
| 735 | AMBP protein precursor ($\alpha_1$-microglobulin) | P02760 | X04225 | 0.23/0.04 | − | − | 3.40/2.50 |
| 741 | AMBP protein precursor ($\alpha_1$-microglobulin) | P02760 | X04225 | 0.44/0.57 | 0.29/0.56 | + | − |

TABLE 4-continued

Identification of regulated protein spots in study group/validation group.

| Spot no | Protein name | Swiss-Prot Acc. No. | EMBL Acc No | Expression ratio or trend of regulation in comparison | | | |
|---|---|---|---|---|---|---|---|
| | | | | C1 vs. C3 | D1 vs. D3 | C1 vs. D1 | C3 vs. D3 |
| 742 | Adiponectin | Q15848 | D45371 | − | + | − | 6.89/4.22 |
| 760 | Complement factor H-related protein 2 precursor | P36980 | | 0.20/0.44 | − | − | + |
| 771 | Complement C3 precursor, α chain | P01024 | K02765 | − | 0.43/0.54 | + | − |
| 781 | Complement C3 precursor, α-chain | P01024 | K02765 | 0.51/0.75 | − | − | − |
| 781 | Complement C4 precursor, acidic or basic C4 | P01028 | | 0.51/0.75 | − | − | − |
| 785 | Complement factor D precursor | P00746 | M84526 | 0.31/0.56 | 0.53/0.54 | − | + |
| 786 | Complement factor D precursor | P00746 | M84526 | — | 0.18/0.21 | − | + |
| 825 | Plasma retinol-binding protein precursor | P02753 | X00129; BC020633 | 0.26/0.40 | — | + | + |
| 826 | Plasma retinol-binding protein precursor | P02753 | See above | 0.27/0.18 | 0.33/0.47 | + | + |
| 847 | β$_2$-glycoprotein I precursor (Apolipoprotein H) | P02749 | See above | 0.39/0.71 | — | − | + |
| no. up-regulated spots | | 4 | | | | − | 9 |
| no. down-regulated spots | | 22 | | | | 9 | − |
| total no. of regulated spots | | 26 | | | | 9 | 9 |

TABLE 5

Identification of regulated protein spots in study group.

| Spot no | Protein name | Swiss-Prot/[EMBL] Acc. No. | Expression ratio in comparison | | | |
|---|---|---|---|---|---|---|
| | | | C1 vs. C2 | C2 vs. C3 | D1 vs. D2 | D2 vs. D3 |
| 56 | Ceruloplasmin precursor (Ferroxidase) | P00450 [M13699; M13536] | — | — | — | 1.53 |
| 67 | Plasminogen precursor | | 1.74 | — | 1.74 | — |
| 113 | Complement factor B precursor | P00751 | — | — | 2.02 | — |
| 149 | α$_2$-macroglobulin precursor | P01023 | — | — | 1.68 | — |
| 150 | α$_2$-macroglobulin precursor | P01023 | — | — | 1.97 | — |
| 226 | NO PROTEIN FOUND | | — | — | — | 2.59 |
| 232 | NO PROTEIN FOUND | | — | — | — | 0.35 |
| 238 | Inter-α-trypsin inhibitor heavy chain H1 precursor | P19827 | — | — | — | 0.31 |
| 242 | Inter-α-trypsin inhibitor heavy chain H1 precursor | P19827 | — | — | — | 0.24 |
| 243 | Inter-α-trypsin inhibitor heavy chain H1 precursor | P19827 | — | — | 4.09 | 0.12 |
| 249 | NO PROTEIN FOUND | | 2.40 | — | — | — |
| 288 | NO PROTEIN FOUND | | — | — | 0.49 | — |
| 291 | Complement component C9 precursor | P02748 | — | — | 0.61 | — |
| 352 | Hemopexin precursor (β$_{1B}$-glycoprotein) | P02790 | — | 1.57 | — | — |
| 381 | Hemopexin precursor (β$_{1B}$-glycoprotein) | P02790 | — | 0.60 | — | — |
| 418 | NO PROTEIN FOUND | | — | 0.38 | — | — |
| 430 | NO PROTEIN FOUND | | — | 0.31 | — | — |
| 442 | Kininogen-1 precursor | P01042 | — | 0.64 | — | — |
| 448 | NO PROTEIN FOUND | | — | — | 0.57 | — |

TABLE 5-continued

Identification of regulated protein spots in study group.

| Spot no | Protein name | Swiss-Prot/[EMBL] Acc. No. | C1 vs. C2 | C2 vs. C3 | D1 vs. D2 | D2 vs. D3 |
|---|---|---|---|---|---|---|
| 463 | Complement C1r subcomponent precursor | P00736 | — | — | — | 0.31 |
| 464 | Complement C1r subcomponent precursor | P00736 | — | — | 20.64 | 0.04 |
| 466 | $\beta_2$-glycoprotein I precursor (Apolipoprotein H) | P02749 | 0.31 | — | — | — |
| 498 | NO PROTEIN FOUND | | — | — | 3.20 | 0.33 |
| 510 | Hemopexin precursor ($\beta_{1B}$-glycoprotein) | P02790 | — | — | 2.02 | 0.65 |
| 515 | Hemopexin precursor ($\beta_{1B}$-glycoprotein) | P02790 | — | — | — | 0.42 |
| 551 | Hemopexin precursor ($\beta_{1B}$-glycoprotein) | P02790 | — | — | 1.96 | — |
| 557 | Pigment epithelium-derived factor precursor | P36955 | 0.66 | — | — | — |
| 562 | Leucine-rich $\alpha_2$-glycoprotein precursor | P02750 | — | — | — | 2.73 |
| 570 | Pigment epithelium-derived factor precursor | P36955 | 0.54 | — | — | — |
| 575 | NO PROTEIN FOUND | | — | — | 0.27 | 3.17 |
| 599 | NO PROTEIN FOUND | | 5.65 | — | — | — |
| 622 | Apolipoprotein A-IV precursor | P06727 | — | — | 0.25 | 2.42 |
| 657 | Eukar. translation initiation factor 3 subunit 10 | Q14152 [U58046; U78311] | — | — | — | 1.68 |
| 657 | Ceruloplasmin precursor | P00450 | — | — | — | 1.68 |
| 658 | Ceruloplasmin precursor | P00450 | 2.97 | 0.33 | — | — |
| 667 | NO PROTEIN FOUND | | — | 0.14 | — | — |
| 672 | NO PROTEIN FOUND | | — | — | — | 1.88 |
| 673 | 130 kDa leucine-rich protein | P42704 | — | 0.08 | — | — |
| 702 | NO PROTEIN FOUND | | 0.61 | — | — | — |
| 711 | Complement C4-A precursor | P0C0L4 | — | — | 1.94 | — |
| 711 | Complement C4-B precursor | P0C0L5 | — | — | 1.94 | — |
| 722 | AMBP protein precursor ($\alpha_1$-microglobulin) | P02760 | 0.36 | 0.43 | 0.17 | 6.28 |
| 728 | AMBP protein precursor ($\alpha_1$-microglobulin) | P02760 | 0.26 | 0.15 | 0.06 | 4.30 |
| 730 | AMBP protein precursor ($\alpha_1$-microglobulin) | P02760 | 0.27 | 0.24 | 0.32 | — |
| 734 | AMBP protein precursor ($\alpha_1$-microglobulin) | P02760 | 0.46 | 0.31 | 0.20 | 2.72 |
| 735 | AMBP protein precursor ($\alpha_1$-microglobulin) | P02760 | 0.40 | — | 0.27 | 3.19 |
| 771 | Complement C3 precursor | P01024 | — | — | — | 0.32 |
| 785 | Complement factor D precursor | P00746 | 0.42 | — | 0.27 | — |
| 786 | Complement factor D precursor | P00746 | 0.10 | — | 0.06 | — |
| 825 | Plasma retinol-binding protein precursor | P02753 | — | — | 0.27 | — |
| 826 | Plasma retinol-binding protein precursor | P02753 | 0.40 | — | 0.23 | — |
| 849 | NO PROTEIN FOUND | | — | 0.30 | — | — |
| 854 | $\alpha_{1B}$-glycoprotein precursor | P04217 | — | — | — | 1.51 |
| no. up-regulated spots | | | 4 | 1 | 10 | 12 |
| no. down-regulated spots | | | 12 | 12 | 15 | 10 |
| total no. of regulated spots | | | 16 | 13 | 25 | 22 |

Spot nos. 657, 711 and 781 were assigned to two different proteins (highlighted in grey). 'Spot number' is the spot number assigned in the reference gel from Progenesis. 'Expression ratio' is the quotient of mean normalized spot volumes. $C_1$ vs. $C_2$ means ratio $$\frac{C_2}{C_1}$$

and $C_1$ vs. $C_3$ means ratio $$\frac{C_3}{C_1}.$$

The ratio is given for statistically significant regulations with significance value p<0.005. If the regulation did not meet this value, the trend of regulation is indicated by +/− standing for up-/down-regulation.

Taking all comparisons of the study group in table 4 and 5 together, a total number of 73 individual spots and a total number of 29 individual proteins were identified as regulated. Expression ratio was between 0.04 and 20.64. Coverage of regulated proteins, i.e. percentage of the primary protein sequence which was covered by trypsinated peptides found by PMF, was 3%-66% with a mean value of 29%.

Validation of the Results of the Study Group with the Validation Group

An independent set of 120 plasma samples (validation group) has been analyzed with the same strategy. For each spot found to be regulated in the study group (see table 4 and 5), the regulation was compared with the validation group as presented in table 6. The mean validation rate was 74%.

TABLE 6

Number of regulated spots in study and validation group and validation rate.

| Comparison | Study group | Validation group | Validation rate [%] |
| --- | --- | --- | --- |
| C1 vs. C3 | 26 | 20 | 77 |
| C1 vs. C2 | 16 | 13 | 81 |
| C2 vs. C3 | 13 | 7 | 54 |
| Control (total) | 55 | 40 | 73 |
| D1 vs. D3 | 10 | 10 | 100 |
| D1 vs. D2 | 25 | 19 | 76 |
| D2 vs. D3 | 22 | 12 | 55 |
| Disease (total) | 57 | 41 | 72 |
| C1 vs. D1 | 4 | 2 | 50 |
| C3 vs. D3 | 9 | 8 | 89 |
| Inter (total) | 13 | 10 | 77 |

Functions and Properties of the Regulated Proteins

Below functions and properties of identified proteins are listed according to the Swiss-Prot protein knowledgebase [1].

Inflammatory and Immune-Related Proteins in Alphabetical Order

N-Acetylmuramoyl-L-Alanine Amidase Precursor PGRP2_HUMAN Q96PD5

May play a scavenger role by digesting biologically active peptidoglycan (PGN) into biologically inactive fragments. Has no direct bacteriolytic activity. Strongly expressed in liver and fetal liver, and secreted into serum. Expressed to a much lesser extent in transverse colon, lymph nodes, heart, thymus, pancreas, descending colon, stomach and testis. Isoform 2 is not detected in the liver or serum. PGRP2_HUMAN is involved in the immune response.

C4b-Binding Protein α-Chain Precursor C4BP_HUMAN P04003

Controls the classical pathway of complement activation. It binds as a cofactor to C3b/C4b inactivator (C3bINA), which then hydrolyzes the complement fragment C4b. It also accelerates the degradation of the C4bC2a complex (C3 convertase) by dissociating the complement fragment C2a. Alpha chain binds C4b. It interacts also with anticoagulant protein S and with serum amyloid P component. Found in chylomicrons (large lipoprotein particles) in plasma. C4BP_HUMAN is involved in the complement pathway, which is part of the innate immune system.

Complement C1R Subcomponent Precursor C1R_HUMAN P00736

C1r B chain is a serine protease that combines with C1q and C1s to form C1, the first component of the classical pathway of the complement system. C1R_HUMAN is a component of the complement pathway. It contains a heavy chain and a light chain.

Complement C3 Precursor CO3_HUMAN P01024

C3 plays a central role in the activation of the complement system. Its processing by C3 convertase is the central reaction in both classical and alternative complement pathways. After activation C3b can bind covalently, via its reactive thiolester, to cell surface carbohydrates or immune aggregates. Derived from proteolytic degradation of complement C3, C3a anaphylatoxin is a mediator of local inflammatory process. It induces the contraction of smooth muscle, increases vascular permeability and causes histamine release from mast cells and basophilic leukocytes. CO3_HUMAN is involved in inflammatory response[1]. Processing of CO3_HUMAN by the removal of 4 Arg residues forms two chains, beta and alpha, linked by a disulfide bond.

Complement C4 Precursor CO4A_HUMAN, CO4B_HUMAN P01028

C4 plays a central role in the activation of the classical pathway of the complement system. It is processed by activated C1 which removes from the alpha chain the C4a anaphylatoxin. The remaining alpha chain fragment C4b is the major activation product and is an essential subunit of the C3 convertase (C4b2a) and the C5 convertase (C3bC4b2a) enzymes of the classical complement pathway. Derived from proteolytic degradation of complement C4, C4a anaphylatoxin is a mediator of local inflammatory process. It induces the contraction of smooth muscle, increases vascular permeability and causes histamine release from mast cells and basophilic leukocytes. Human complement component C4 is polymorphic at two loci, C4A and C4B. 13 alleles of C4A and 22 alleles of C4B have been detected. The allele shown here is C4A4. The C4A alleles carry the Rodgers (Rg) while the C4B alleles carry the Chido (Ch) blood group antigens. C4A allotypes react more rapidly with the amino group of peptide antigens while C4B allotypes react more rapidly with the hydroxyl group of carbohydrate antigens. CO4_HUMAN is a component of the complement pathway and the inflammatory response.

Complement Component C9 Precursor CO9_HUMAN P02748

CO9_HUMAN is the final component of the complement system to be added in the assembly of the membrane attack complex. It is able to enter lipid bilayers, forming transmembrane channels. Component of the membrane attack complex which groups the complement plasma glycoproteins C5b, C6, C7, C8 and polymeric C9 on biological membranes. CO9_HUMAN is a component of the complement alternative pathway[2] and the membrane attack complex[3]. Thrombin cleaves CO9_HUMAN to produce C9a and C9b.

Complement Factor B Precursor CFAB_HUMAN P00751

Factor B which is part of the alternate pathway of the complement system is cleaved by factor D into 2 fragments: Ba and Bb. Bb, a serine protease, then combines with complement factor 3b to generate the C3 or C5 convertase. It has also been implicated in proliferation and differentiation of preactivated B-lymphocytes, rapid spreading of peripheral blood monocytes, stimulation of lymphocyte blastogenesis and lysis of erythrocytes. Ba inhibits the proliferation of preactivated B-lymphocytes.

Complement Factor D Precursor CFAD_HUMAN P00746

Factor D cleaves factor B when the latter is complexed with factor C3b, activating the C3bbb complex, which then becomes the C3 convertase of the alternate pathway. Its function is homologous to that of C1s in the classical pathway. CFAD_HUMAN is involved in the complement alternate pathway.

Ig μ Chain C Region MUC_HUMAN P01871
Other Proteins in Alphabetical Order
130 kDa Leucine-Rich Protein LPPRC_HUMAN P42704

Unknown function. Expressed ubiquitously. Expression is highest in heart, skeletal muscle, kidney and liver, intermediate in brain, nonmucosal colon, spleen and placenta, and lowest in small intestine, thymus, lung and peripheral blood leukocytes.

Adiponectin ADIPO_HUMAN Q15848

Important negative regulator in hematopoiesis and immune systems; may be involved in ending inflammatory responses through its inhibitory functions. Inhibits endothelial NF-kappa-B signaling through a cAMP-dependent pathway. Inhibits TNF-alpha-induced expression of endothelial adhesion molecules. Involved in the control of fat metabolism and insulin sensitivity. Synthesized exclusively by adipocytes and secreted into plasma.

AMBP Protein Precursor ($\alpha_1$-Microglobulin) AMBP_HUMAN P02760

AMBP_HUMAN contains 2 chains, α1-microglobulin and inter-α-trypsin inhibitor light chain. α1-microglobulin occurs in many physiological fluids including plasma, urine, and cerebrospinal fluid. It appears not only as a free monomer but also in complexes with IgA and albumin. It is an immunomodulatory protein with a broad spectrum of possible clinical applications and seems a promising marker for evaluation of tubular function. AMBP might be a valuable complement to serum creatinine levels in the evaluation of renal function in renal transplant recipients. Expressed by the liver and secreted in plasma.

Apolipoprotein A-IV Precursor APOA4_HUMAN P06727

May have a role in chylomicrons and VLDL secretion and catabolism. Required for efficient activation of lipoprotein lipase by ApoC-II; potent activator of LCAT. Apoa-IV is a major component of HDL and chylomicrons. Synthesized primarily in the intestine and secreted in plasma.

Ceruloplasmin Precursor CERU_HUMAN P00450

Ceruloplasmin is a blue, copper-binding (6-7 atoms per molecule) glycoprotein. It has ferroxidase activity oxidizing iron(II) to iron(III) without releasing radical oxygen species. It is involved in iron transport across the cell membrane.

Complement Factor H-Related Protein 2 Precursor FHR2_HUMAN P36980

Might be involved in complement regulation. Can associate with lipoproteins and may play a role in lipid metabolism. Expressed by the liver and secreted in plasma.

Eukaryotic Translation Initiation Factor 3 Subunit 10 IF3A_HUMAN Q14152

Binds to the 40S ribosome and promotes the binding of methionyl-tRNAi and mRNA.

$\alpha_{1B}$-Glycoprotein Precursor A1BG_HUMAN P04217

Function not known.

$\beta_2$-Glycoprotein I Precursor (Apolipoprotein H) APOH_HUMAN P02749

Binds to various kinds of negatively charged substances such as heparin, phospholipids, and dextran sulfate. May prevent activation of the intrinsic blood coagulation cascade by binding to phospholipids on the surface of damaged cells. It is expressed by the liver and secreted in plasma.

Hemopexin Precursor ($\beta_{1B}$-Glycoprotein) HEMO_HUMAN P02790

Binds heme and transports it to the liver for breakdown and iron recovery, after which the free hemopexin returns to the circulation. Expressed by the liver and secreted in plasma.

Heparin Cofactor II Precursor HEP2_HUMAN P05546

Thrombin inhibitor activated by the glycosaminoglycans, heparin or dermatan sulfate. In the presence of the latter, HC-II becomes the predominant thrombin inhibitor in place of antithrombin III (AT-III). Also inhibits chymotrypsin, but in a glycosaminoglycan-independent manner. Expressed predominantly in liver.

Inter-α-Trypsin Inhibitor Heavy Chain H1 Precursor ITIH1_HUMAN P19827

May act as a carrier of hyaluronan in serum or as a binding protein between hyaluronan and other matrix protein, including those on cell surfaces in tissues to regulate the localization, synthesis and degradation of hyaluronan which are essential to cells undergoing biological processes. Contains a potential peptide which could stimulate a broad spectrum of phagocytotic cells.

Kininogen-1 Precursor KNG1_HUMAN P01042

(1) Kininogens are inhibitors of thiol proteases; (2) HMW-kininogen plays an important role in blood coagulation by helping to position optimally prekallikrein and factor XI next to factor XII; (3) HMW-kininogen inhibits the thrombin- and plasmin-induced aggregation of thrombocytes; (4) the active peptide bradykinin that is released from HMW-kininogen shows a variety of physiological effects: (4A) influence in smooth muscle contraction, (4B) induction of hypotension, (4C) natriuresis and diuresis, (4D) decrease in blood glucose level, (4E) it is a mediator of inflammation and causes (4E1) increase in vascular permeability, (4E2) stimulation of nociceptors (4E3) release of other mediators of inflammation (e.g. prostaglandins), (4F) it has a cardioprotective effect (directly via bradykinin action, indirectly via endothelium-derived relaxing factor action); (5) LMW-kininogen inhibits the aggregation of thrombocytes; (6) LMW-kininogen is in contrast to HMW-kininogen not involved in blood clotting. It is a secreted protein Leucine-Rich $\alpha_2$-Glycoprotein Precursor A2GL_HUMAN P02750

It is a protein secreted in plasma.

α2-Macroglobulin Precursor A2MG_HUMAN P01023

Is able to inhibit all four classes of proteinases by a unique 'trapping' mechanism. This protein has a peptide stretch, called the 'bait region' which contains specific cleavage sites for different proteinases. When a proteinase cleaves the bait region, a conformational change is induced in the protein which traps the proteinase. The entrapped enzyme remains active against low molecular weight substrates (activity against high molecular weight substrates is greatly reduced).

Following cleavage in the bait region a thioester bond is hydrolyzed and mediates the covalent binding of the protein to the proteinase Pigment epithelium-derived factor precursor PEDF_HUMAN P36955

Neurotrophic protein; induces extensive neuronal differentiation in retinoblastoma cells. Potent inhibitor of angiogenesis. As it does not undergo the S (stressed) to R (relaxed) conformational transition characteristic of active serpins, it exhibits no serine protease inhibitory activity. It is a secreted protein and is found in retinal pigment epithelial cells and blood plasma.

Plasma Retinol-Binding Protein Precursor RETBP_HUMAN P02753

Delivers retinol from the liver stores to the peripheral tissues. In plasma, the RBP-retinol complex interacts with transthyretin, this prevents its loss by filtration through the kidney glomeruli. It is a secreted protein.

Plasminogen Precursor PLMN_HUMAN P00747

Plasmin, formed by conversion from plasminogen, dissolves the fibrin of blood clots and acts as a proteolytic factor in a variety of other processes including embryonic development, tissue remodeling, tumor invasion, and inflammation; inovulation it weakens the walls of the Graafian follicle. It activates the urokinase-type plasminogen activator, collagenases and several complement zymogens, such as C1 and C5. It cleaves fibrin, fibronectin, thrombospondin, laminin and von Willebrand factor. Its role in tissue remodeling and tumor invasion may be modulated by CSPG4. It is a secreted protein and is present in plasma and many other extracellular fluids. It is synthesized in the kidney.

Transthyretin Precursor TTHY_HUMAN (syn Prealbumin) P02766

Thyroid hormone-binding protein. Probably transports thyroxine from the bloodstream to the brain. It is a secreted protein. Most abundant in the choroid plexus and also present in the liver. About 40% of plasma transthyretin circulates in a tight protein-protein complex with the plasma retinol-binding protein (RBP). The formation of the complex with RBP stabilizes the binding of retinol to RBP and decreases the glomerular filtration and renal catabolism of the relatively small RBP molecule.

Conclusion

In this study a set of proteins was identified as biomarker candidates. Results from the study group and the validation group showed an excellent correlation in protein regulation which proves the high quality of the serum sample set and the proteomics procedure.

Time Course of Protein Regulations

Histograms of the time course of protein regulations from disease and control samples of point in time 1, 2 and 3 show three striking regulations, namely Ig µ chain C region (spot no. 210, 213 and 214), pigment epithelium-derived factor precursor (spot no. 570) and AMBP protein precursor ($\alpha_1$-microglobulin) (spot no. 722, 728, 730 and 735). Ig µ level steadily increases in healthy recipients whereas it increases from point in time 1 to 2 and decreases again from point in time 2 to 3 in rejecting recipients. Pigment epithelium-derived factor precursor and $\alpha_1$-microglobulin levels steadily decrease in healthy recipients whereas they decrease from point in time 1 to 2 and increase again from point in time 2 to 3 in rejecting recipients. The same expression profile is observed with spots no. 445, 461, 562, 657, 734, 785, 825, 826, 854 and 862 (see table 4 and 5).

Biomarker Candidates

From the individual comparisons and the time course regulations 16 biomarker candidates could be identified (Swiss-Prot/EMBL protein/nucleic acid database accession numbers are given):
N-acetylmuramoyl-L-alanine amidase precursor Q96PD5/AF384856
Adiponectin Q15848/D45371
AMBP protein precursor ($\alpha_1$-microglobulin) P02760/X04225
C4b-binding protein α-chain precursor P04003/M31452; BC022312
Ceruloplasmin precursor P00450/M13699; M13536
Complement C3 precursor P01024/K02765
Complement component C9 precursor P02748/BC020721; K02766
Complement factor D precursor P00746/M84526
$\alpha_{1B}$-glycoprotein P04217/AF414429; BC035719
$\beta_2$-glycoprotein I precursor P02749/X58100; X53595; X57847; M62839; S80305; BC020703; BC026283
Heparin cofactor II precursor P05546/M12849; X03498
Ig µ Chain C region protein P01871/X17115
Leucine-rich $\alpha_2$-glycoprotein precursor P02750/AF403428; BC034389; BC070198
Pigment epithelium-derived factor precursor P36955/M76979; AF400442
Plasma retinol-binding protein precursor P02753/X00129; BC020633
Translation initiation factor 3 subunit 10 Q14152/U58046; U78311

Conclusion 240 serum samples of kidney transplant recipients were submitted to 2DE proteomic procedure in order to identify novel biomarker candidates for early detection of renal rejection. The clear correlation of the results of the study group and the validation group shows the robustness and reproducibility of our proteomics procedure, especially serum sample preparation by chromatographic immunoaffinity depletion of six high abundant proteins which is commercially available only since 2003, as well as the high quality of the serum sample set. 29 proteins were found regulated between the three selected conditions of renal transplant recipients, 20 of which are related to inflammatory and immune response during renal rejection or renal disease. As a result, 16 proteins could be identified as novel biomarker candidates.

Statistical Analysis of the 2D Gel Data with SIMCA-P.

Data Pre-Processing

The normalised and background-corrected spot data were exported from ProGenesis to Excel and automatically arranged into a format suitable by an in house-developed programme for further analysis. For each comparison of control and treated data, the number of spots in each group, the mean value, the coefficient of variation and two-tailed Student's t-test and Mann-Whitney Test computed by StatistiXL (Version 1.5) were automatically generated. In parallel, the data were imported into SIMCA-P software (version 11; Umetrics) and the spot data assessed to determine whether any spots required pre-processing prior to further analysis. For the spot data (variables), two different scaling methods were evaluated; Unit variance (UV) and Pareto (Par). UV is the default scaling method and Pareto scaling is in between no scaling and UV scaling and gives the variable a variance equal to its standard deviation instead of unit variance. Three different transformation methods were evaluated; no transformation, automatic transformation and $Log_{10}$ transformation. By default, there is no transformation, the automatic transformation is performed by the software which checks if variables need a log transformation and if so it applies it. The $Log_{10}$ transformation is applied to spots that are positively skewed (>0.7) to give distributions closer to normal. The optimal goodness-of-fit ($R^2$) and cumulative goodness-of-prediction ($Q^2$[cum]) parameters were obtained with the combination of the UV scaling method with an automatic transformation for the control (C gels) and disease gels (C gels) as shown in Table 7.

TABLE 7

Scaling and transformation methods tested for the variables.

| Model | number of component | Transformation | Scaling | R2X | R2Y | Q2(cum) |
|---|---|---|---|---|---|---|
| PCA with C gels | 4 | no transformation | UV | 0.354 | x | 0.0682 |
| PCA with C gels | 3 | no transformation | Pareto | 0.322 | X | 0.0456 |
| PCA with C gels | 4 | Automatic | UV | 0.398 | X | 0.0846 |
| PCA with C gels | 3 | Log10 | UV | 0.336 | X | 0.0923 |
| PCA with C-2 gels | 5 | Automatic | UV | 0.439 | X | 0.0838 |
| PCA with D gels | 3 | no transformation | UV | 0.303 | X | 0.08 |
| PCA with D gels | 3 | no transformation | Pareto | 0.339 | X | 0.0705 |
| PCA with D gels | 4 | Automatic | UV | 0.41 | X | 0.127 |
| PCA with D gels | 4 | Automatic | Pareto | 0.41 | X | 0.0951 |
| PCA with D gels | 4 | Log10 | Pareto | 0.402 | X | 0.0852 |

There were two kinds of analysis performed. Initially, an unsupervised method called principal components analysis (PCA) was applied to all experimental groups. Then secondly, a supervised method called partial least squares—discriminant analysis (PLS-DA) was applied to the four data sets comparing the Control −1 versus Control −3; Disease −1 versus Disease −3; Control −1 versus Disease −1 and Control −3 versus Disease −3 to find out whether any differences could be found to distinguish between sample groups.

PCA Analysis of the Control Data Set

Principal component Analysis (PCA) is a multivariate projection method designed to extract and display the systematic variation in the data matrix (gels and spot volumes in our case). With PCA analysis, a number of diagnostic and interpretation tools are available.

Figure 8:
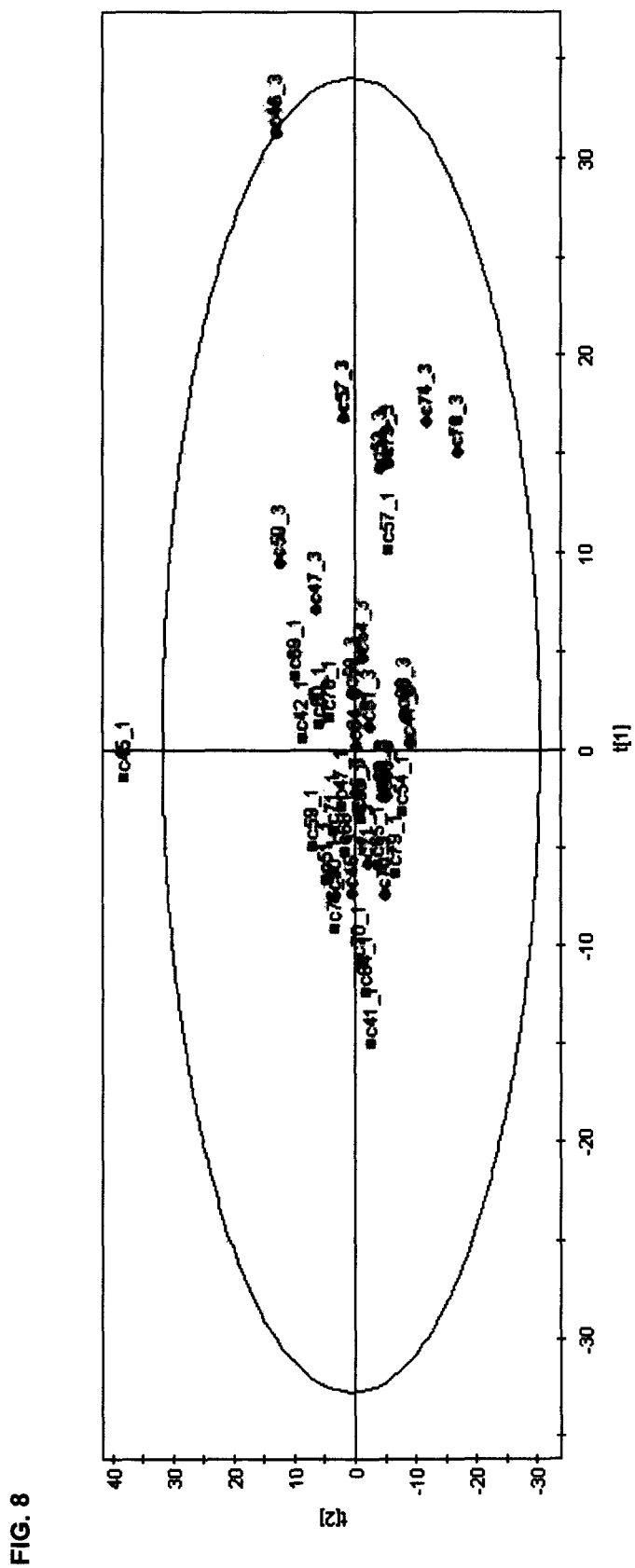

A four component model was auto-fitted to the control data set. The model parameters were as follows: goodness-of-fit ($R^2$)=0.398 and the cumulative goodness-of-prediction ($Q^2$[cum])=0.0846. FIG. 8 shows the observations scores of the model.

Figure 9:
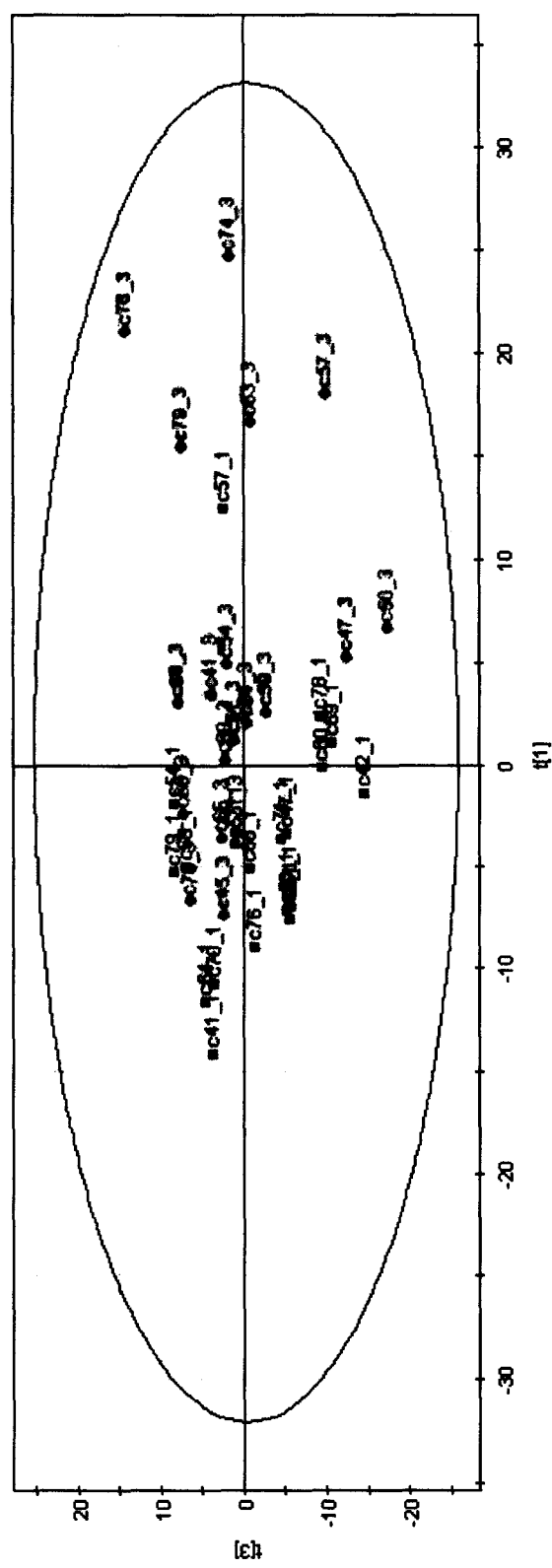
FIG. 9 PCA scores plot of the control data set without the outliers gels.

We can observe in the FIG. 8 that two gels are located outside the ellipse and could be considered as strong outliers (C45_1 and C46_3). We removed these two gels and a new model with five components was fitted (see Table 7). The model parameters were as follows: $R^2$=0.439 and $Q^2$[cum]=0.0838. FIG. 9 shows the observations scores of the model.

Although the goodness-of-fit ($R^2$) parameter indicates that 44% of the total variance in the data are explained, the low value for the $Q^2$ suggests that the model is not very robust. As shown in FIG. 9, it is clear that the model does not display clusters between the gels in the group. A typical clustering model may display two groups, one corresponding to the control_1 gels and the second to the control_3 gels.

PCA Analysis of the Disease Data Set

Figure 10:
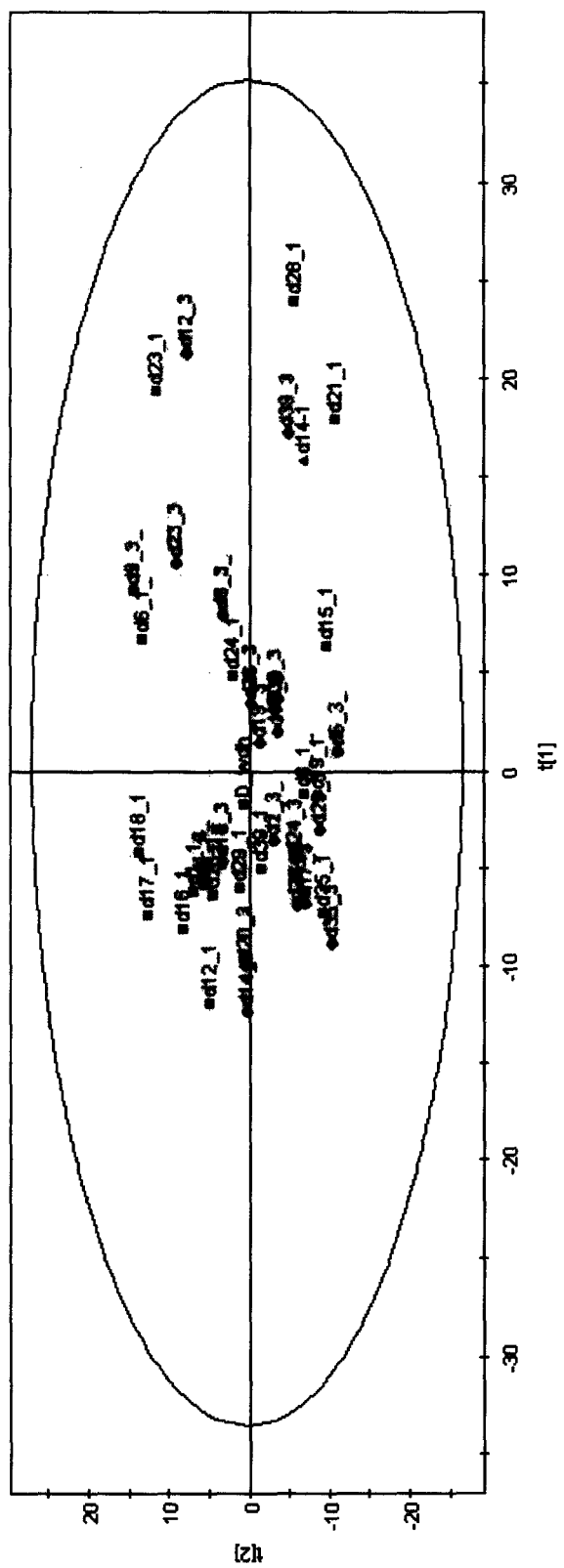
FIG. 10 PCA scores plot of the disease data set containing all gels.

A four component model was auto-fitted to the control data set. The model parameters were as follows: goodness-of-fit ($R^2$)=0.41 and the cumulative goodness-of-prediction ($Q^2$[cum])=0.127. FIG. 10 shows the observations of the model.

Although the goodness-of-fit ($R^2$) parameter indicates that 41% of the total variance in the data are explained, the low value for the $Q^2$ suggests that the model is not very robust. As shown in FIG. 10, we do not observe outliers, nor does the model display clusters between the gels in the group.

For the two models, we observe low values for $R^2$ and near-zero values for $Q^2$ leading us to conclude that these models are not well explained or predicted. Even if low values are already observed for 2D gel data, especially related to human sample analysis, potential explanations are the samples themselves (high biological heterogeneity) and/or sample treatments (freeze-thaw cycles, depletion, 2D gel electrophoresis).

PLS-DA of the Control Data Set

The Partial Least Squares—Discriminant Analysis (PLS-DA) is a method for relating two data matrices, X (gels) and Y (spot volume), to each other by a linear multivariate model. This type of analysis is appropriate to determine whether any differences could be found to discriminate between the control_1 group (blood taken during transplantation) and control_3 group (blood taken when the transplantation has been validated).

Figure 11:
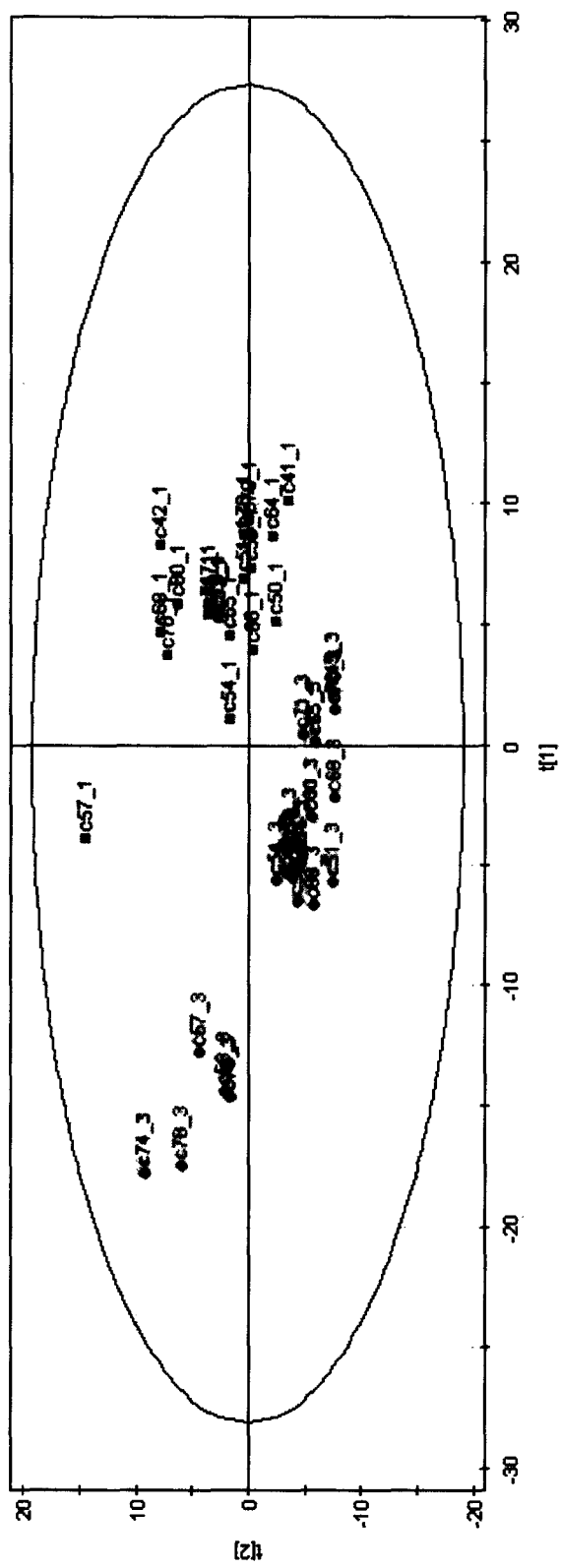
FIG. 11 PLS-DA scores plot of the Control/1 and Control/3 groups.

A two component model was auto-fitted to the control gels data set. The parameters were as follows: $R^2X$=0.185; $R^2Y$=0.898 and $Q^2$=0.431. The additional parameter $R^2Y$ described the goodness-of-fit to the Y-data containing the class of observations. The observations of the scores in the two PLS components of the model are displayed in FIG. 11. The value of $Q^2$ close to 0.5 could be considered as good. As seen in FIG. 11, the separation of the groups appears excellent.

Figure 12:
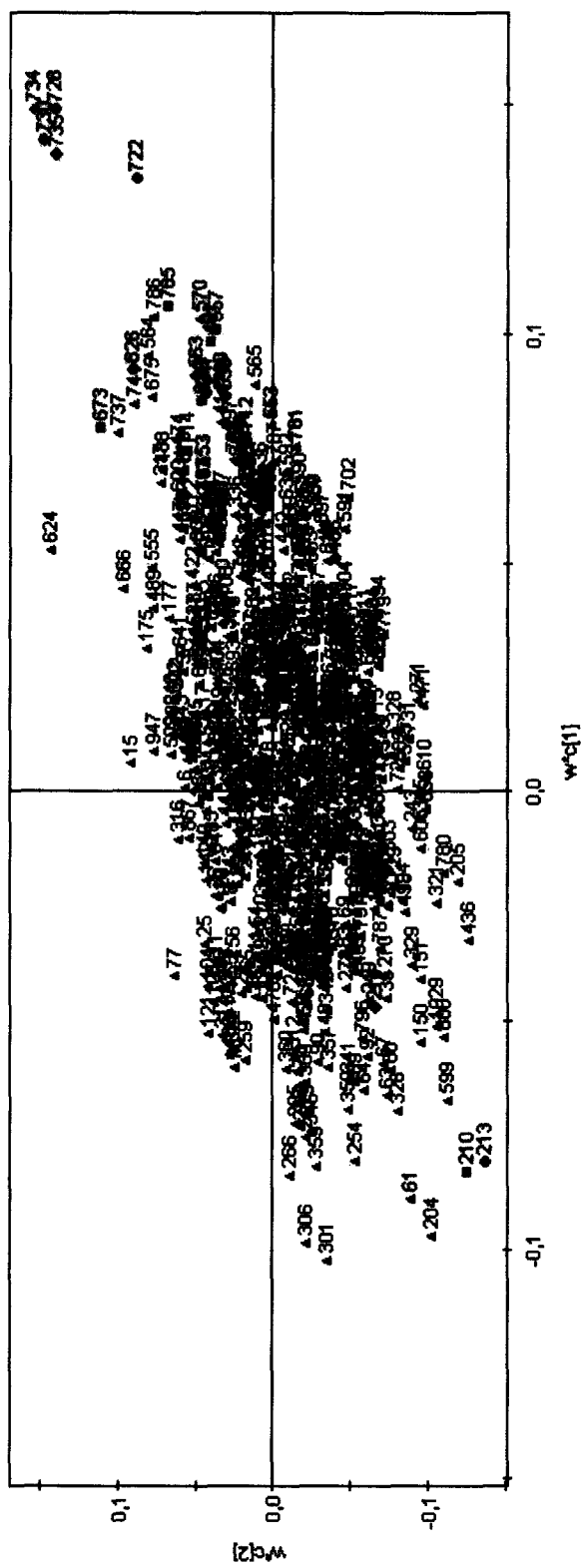
FIG. 12 PLS-DA loading plots (spot numbers) of the Control__1 and Control__3 groups. In lighter type are indicated numbers of spots which have been selected through the 2D gel approach.

The loading plots of this PLS model are displayed in FIG. 12. In lighter type are indicated the number of spots selected through the univariate approach. The plots at the extremes of the horizontal axis describe the differences between the groups. We can observe in FIG. 12 that the lighter type numbers are located at the extremes of the axis which reinforces the fact that these spots may reflect a significant discrimination between the two groups compared. This observation shows a good correlation between the univariate and multivariate approaches as well.

PLS-DA of the Disease Data Set

We applied this type of analysis to determine whether any differences could be found to discriminate between the disease_1 group (blood taken during transplantation) and disease_3 group (blood taken when the transplantation has been rejected).

Figure 13:
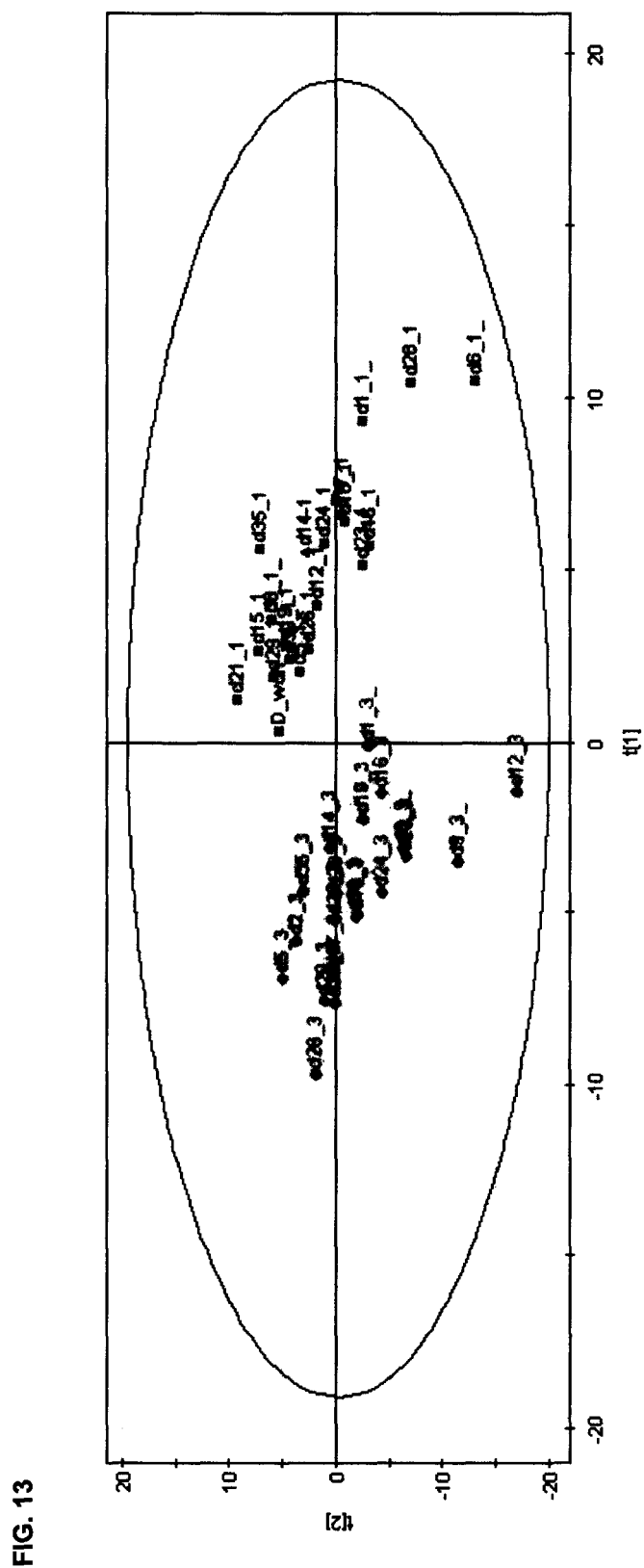
FIG. 13 PLS scores plots of the Disease/1 and Disease/3 groups.

A two component model was auto-fitted to the control gels data set. The parameters were as follows: $R^2X$=0.143; $R^2Y$=0.902 and $Q^2$=0.301. The observations of the scores in the two PLS components of the model are displayed in FIG. 13. As seen in FIG. 13, the separation of the groups appears excellent.

Figure 14:
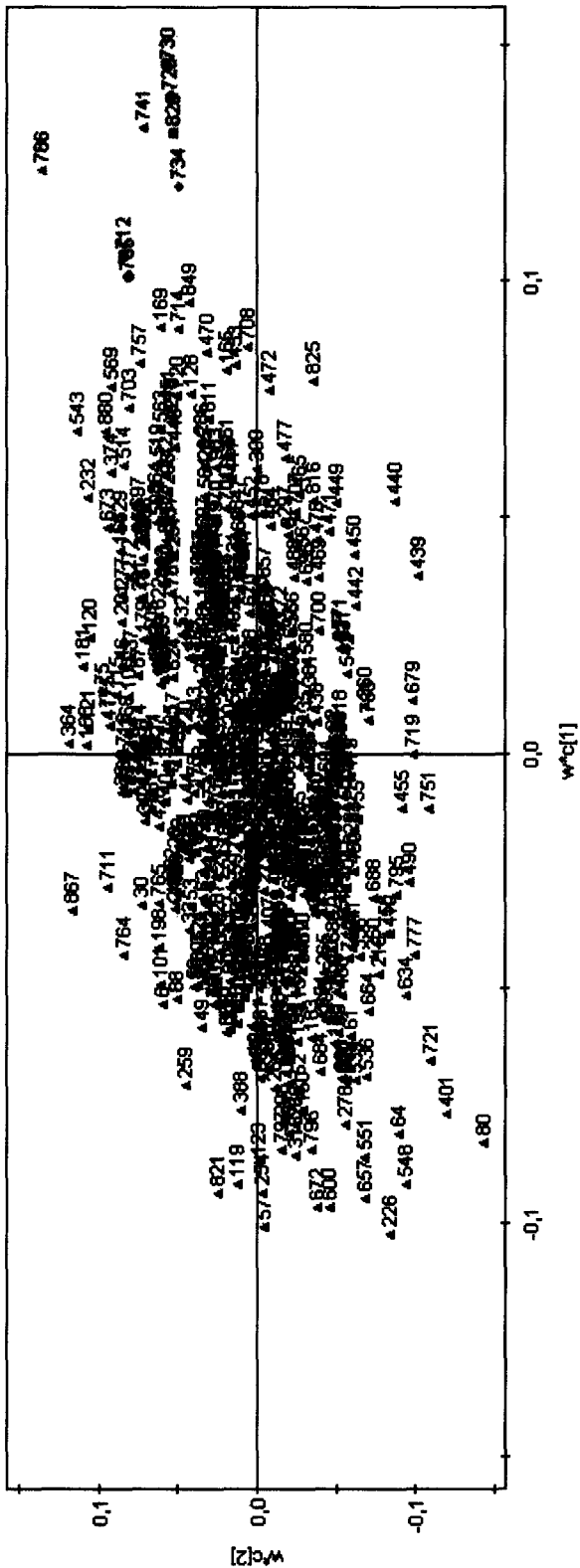
FIG. 14 PLS-DA loading plots (spot numbers) of the Disease/1 and Disease/3 groups. In lighter type are indicated numbers of spots which have been selected through the 2D gel approach.

The loading plots of this PLS model are displayed in FIG. 14. In lighter type are indicated the number of spots selected through the 2D gel approach. We can observe in FIG. 14 that the lighter type numbers are located at the extremes of the axis which reinforces the fact that these spots may reflect a significant discrimination between the two groups compared. This observation shows a good overlap between the univariate and multivariate approaches as well.

Analysis of the Data Set Containing Control_1 and Disease_1 ("Sample_1") Groups

PCA Analysis of the Sample_1 Data Set

Figure 15:
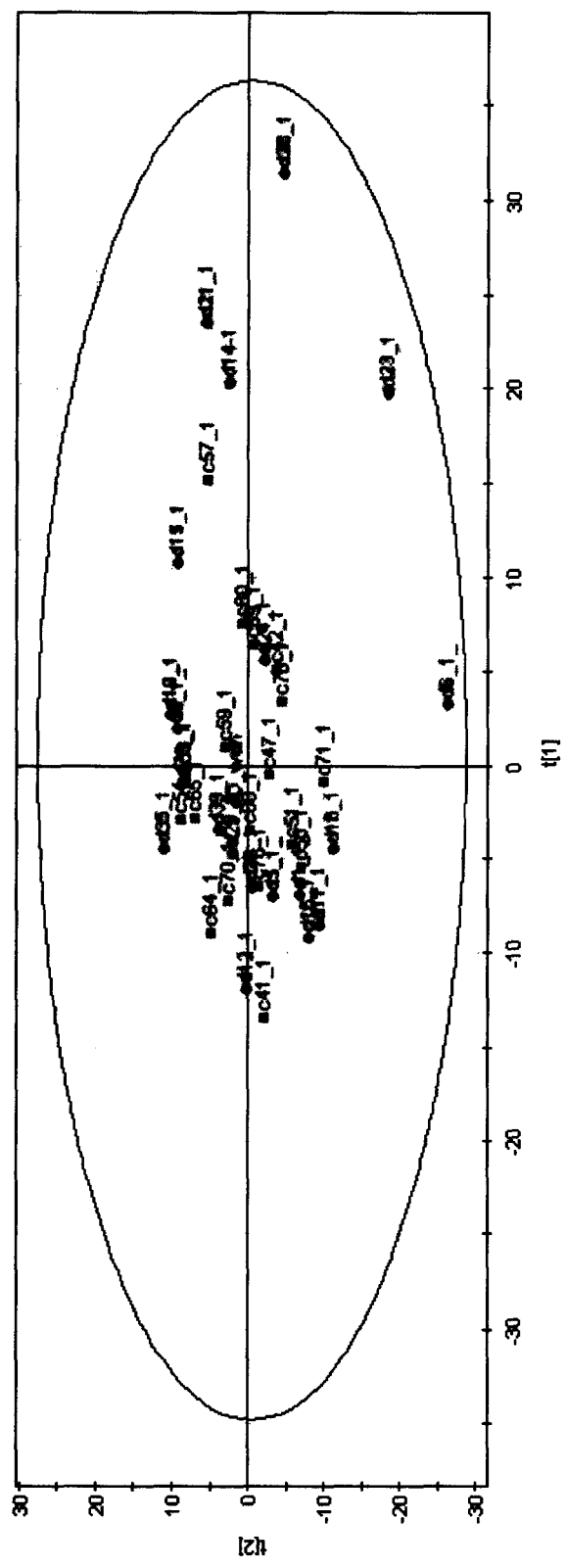
FIG. 15 PCA score plots of the control/1 and disease/1 groups.

A six component model was auto-fitted to the control data set. The model parameters were as follows: goodness-of-fit ($R^2$)=0.481 and the cumulative goodness-of-prediction ($Q^2$[cum])=0.0519. FIG. 15 shows the observations plots of the model.

Although the goodness-of-fit ($R^2$) parameter indicates that 48% of the total variance in the data are explained, the low value for the $Q^2$ suggests that the model is not very robust. As shown in FIG. 15, we do not observe strong outliers, nor does the model display clusters between the gels in the group.

PLS-DA Analysis of the Sample_1 Data Set

Figure 16:
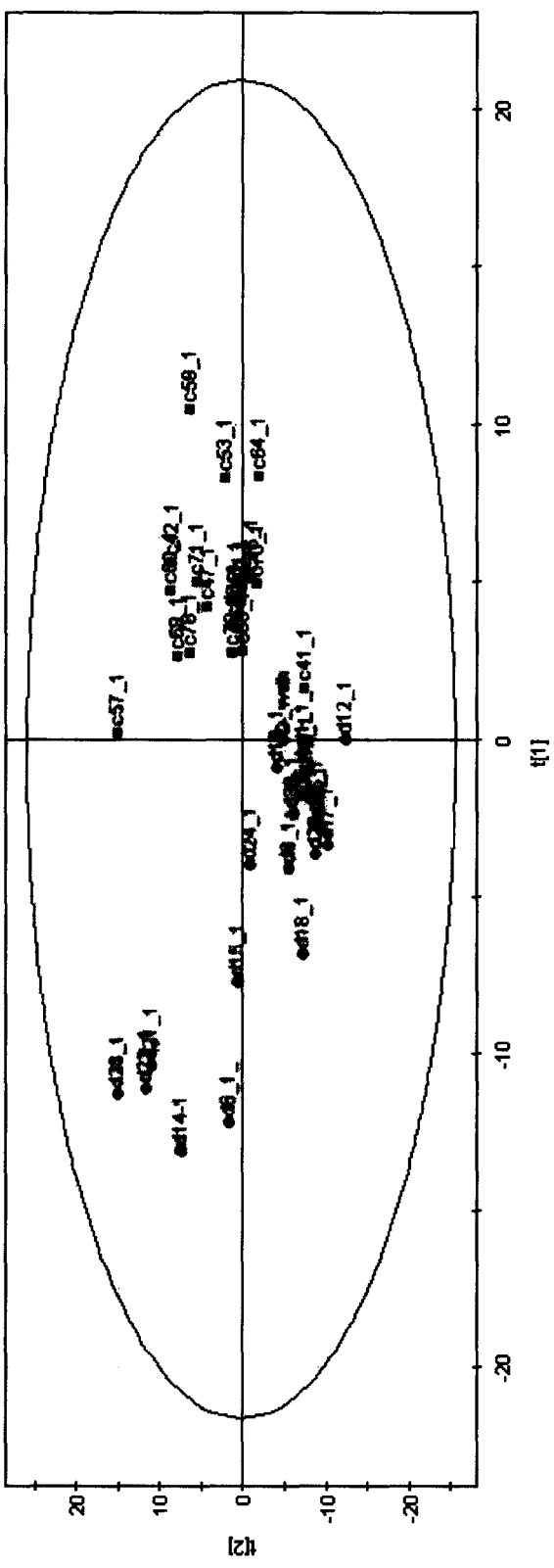
FIG. 16 PLS scores plots of the sample/1 data set.

A two component model was auto-fitted to the data set. The parameters were as follows: $R^2X$=0.199; $R^2Y$=0.828 and $Q^2$=0.148. The observations of the scores in the two PLS components of the model are displayed in FIG. 16. As seen in FIG. 16, the separation of the groups appears excellent.

Figure 17:
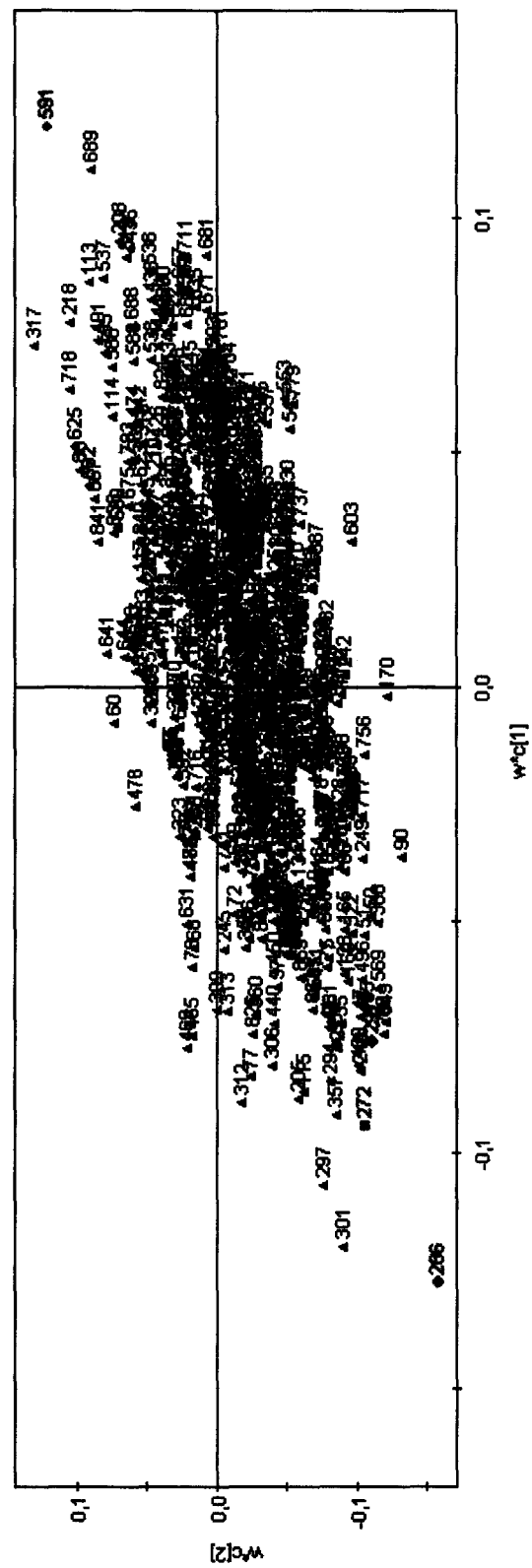
FIG. 17 PLS loadings plots of the sample/1 groups. In lighter type are indicated numbers of spots which have been selected through the 2D gel approach.

The loading plots of this PLS model are displayed in FIG. 17. In lighter type are indicated the number of spots selected through the 2D gel approach. We can observe in FIG. 17 that the lighter type numbers are located at the extremes of the axis which reinforces the fact that these spots may reflect a significant discrimination between the two groups compared. This observation shows a good overlap between the statistical and 2D gel electrophoresis approaches as well.

Analysis of the Data Set Containing Control_3 and Disease_3 ("Sample_3") Groups

PCA Analysis of the Sample_3 Data Set

Figure 18:
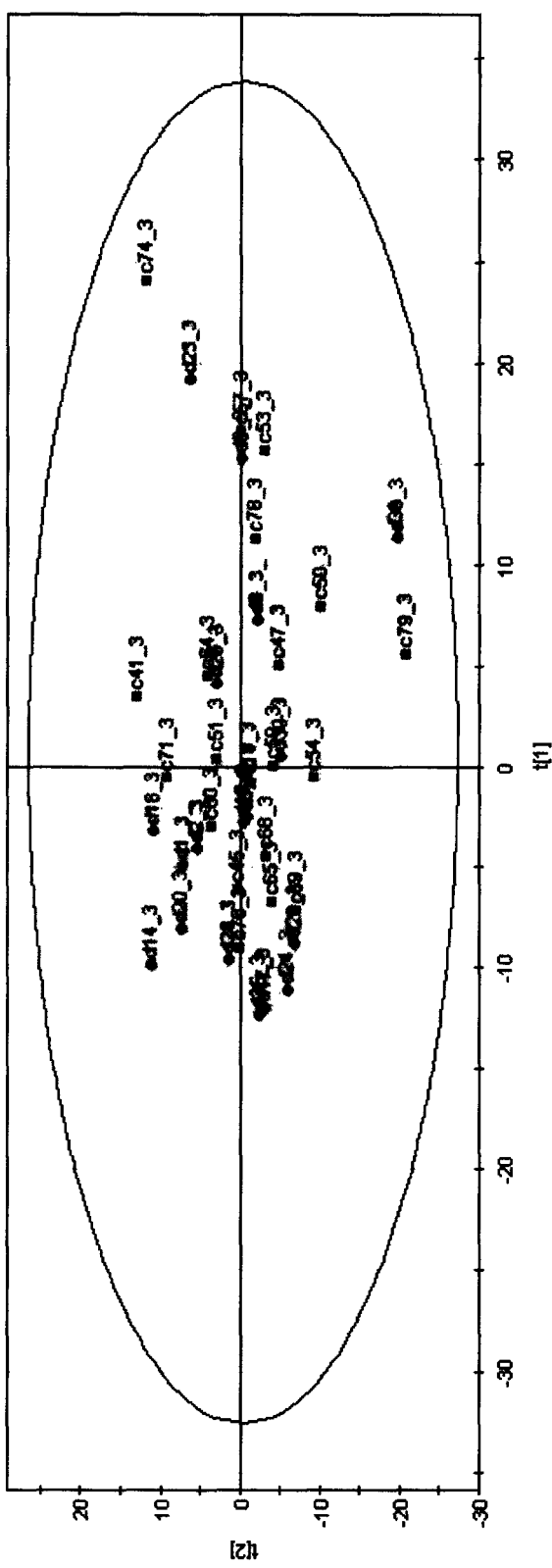
FIG. 18 PCA score plots of the control/3 and disease/3 groups.

During a preliminary analysis with all gels from sample_3 set, we observed a strong outlier (gel D12_3, data not shown). Consequently, we removed the gel from the analysis and performed a new one. A six component model was auto-fitted to the sample_3 data set. The model parameters are $R^2$=0.488 and $Q^2$=0.0757. The observation scores for the two PCA components of this model are displayed in FIG. 18.

The low values for $R^2$ and $Q^2$ suggest that the model is not particularly robust. It is clear from the examining the positions of the gels in the first two components that there is no pattern of clustering between observations in this data set.

PLS-DA Analysis of the Sample_3 Data Set

Figure 19:
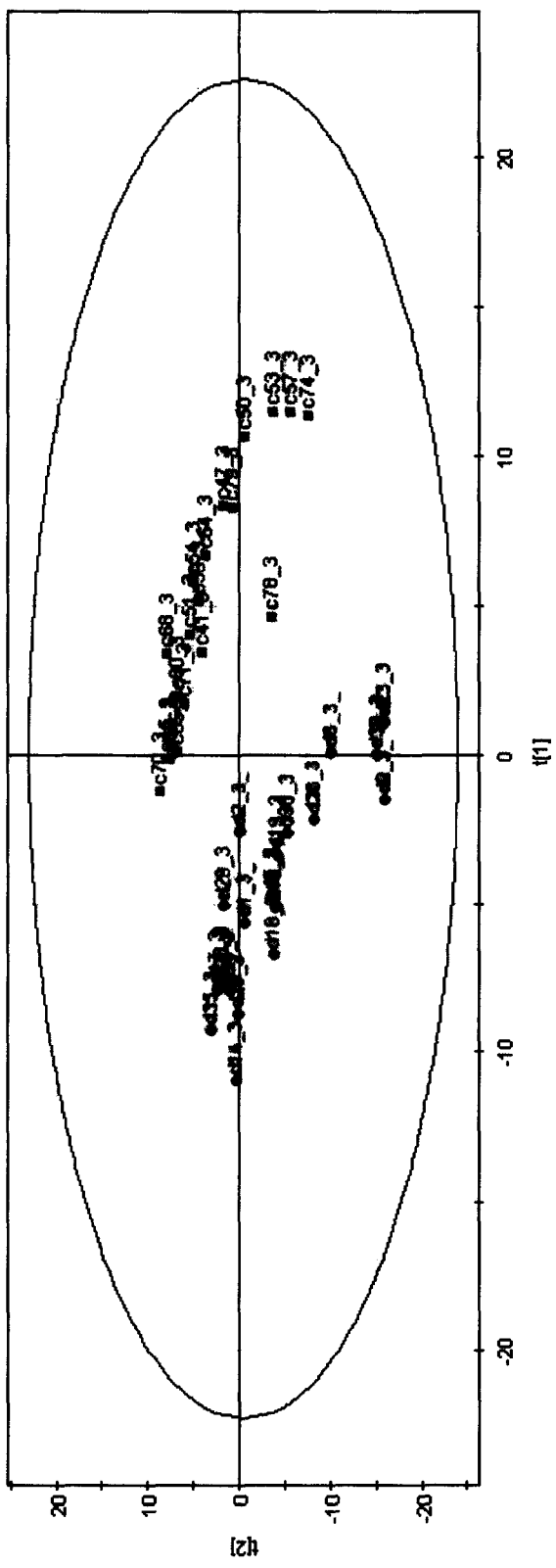
FIG. 19 PLS score plots of gels from the sample/3 data set.

A four component model was auto-fitted to the data set. The parameters were as follows: $R^2X$=0.302; $R^2Y$=0.992 and $Q^2$=0.725. Generally, a $Q^2$>0.7 is regarded as very good. The observations of the scores in the two PLS components of the model are displayed in FIG. 12. As seen in FIG. 19, the separation of the groups appears excellent.

Figure 20:
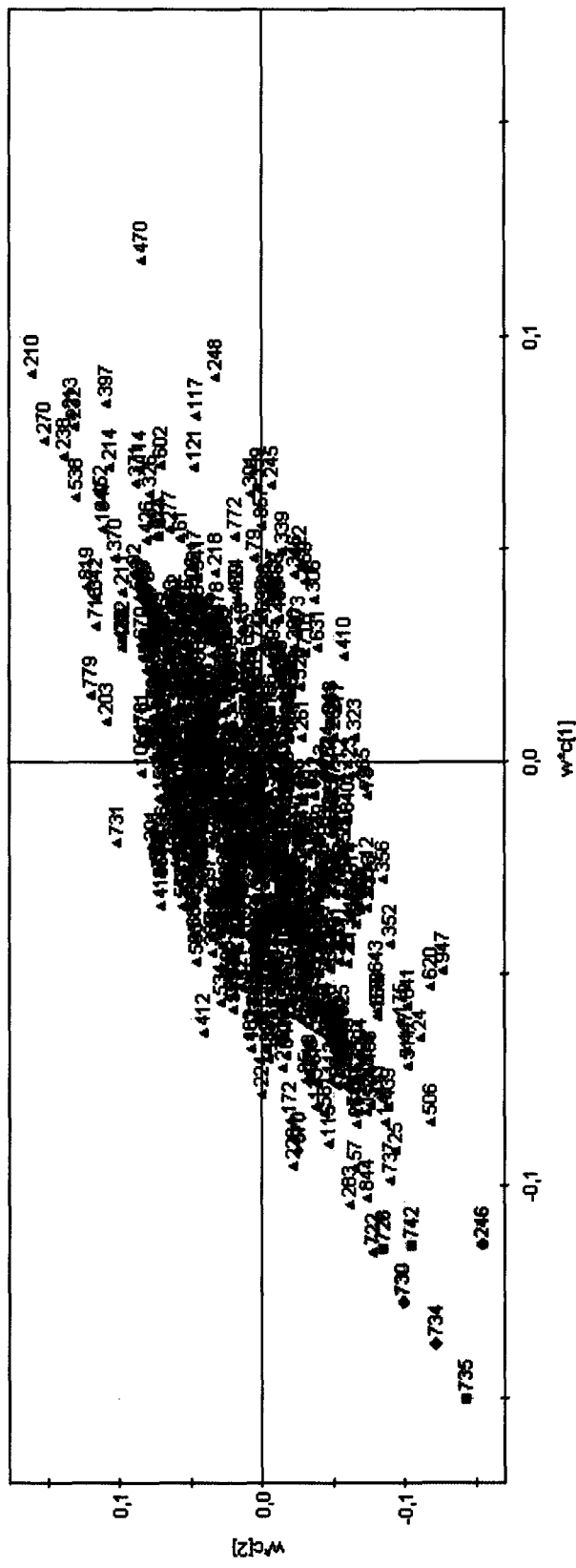
FIG. 20 PLS loading plots from the sample/3 data set. In lighter type are indicated numbers of spots selected through the 2D gel approach.

The loading plots of this PLS model are displayed in FIG. 20. In lighter type are indicated the number of spots selected through the 2D gel approach. We can observe in FIG. 20 that the lighter type numbers are located at the extremes of the axis which reinforces the fact that these spots may reflect a significant discrimination between the two groups compared. This observation shows a good overlap between the statistical and 2D gel electrophoresis approaches as well.

The invention claimed is:

1. A method for the diagnosis and/or prognosis of renal damage in a human patient, said renal damage being caused by chronic transplant rejection following renal transplantation, the method comprising (i) detecting the presence or amount of an autoantibody against at least one marker protein in a sample from said patient, said autoantibody being at least one of an IgG autoantibody and an IgM autoantibody, said sample being selected from the group consisting of a renal tissue sample, a blood sample, a serum sample, a plasma sample and a urine sample; (ii) comparing the detected autoantibody to a control sample, wherein the presence or altered amount of said at least one marker protein in said patient sample, as represented by said detected presence or amount of the autoantibody, in comparison to said autoantibody level in said control sample, is indicative of said renal damage in said patient, and wherein said at least one marker protein is selected from the group consisting of Ig μ chain C region protein; C4b-binding protein α-chain precursor; heparin cofactor II precursor; N-acetylmuramoyl-L-alanine amidase precursor; complement component C9 precursor; β2-glycoprotein I precursor; leucine-rich $α_2$-glycoprotein precursor; complement C3 precursor; AMBP protein precursor (α-1-microglobulin); adiponectin; complement factor D precursor; ceruloplasmin precursor (ferroxidase); pigment epithelium-derived factor precursor; translation initiation factor 3 subunit 10; plasma retinol-binding protein precursor; $α_{1B}$-glycoprotein.

2. The method of claim 1, wherein the renal damage is caused by chronic allograft nephropathy.

3. The method of claim 2, wherein said marker protein is N-acetylmuramoyl-L-alanine amidase precursor.

4. The method of claim 1, wherein the method comprises the steps of:
    (a) contacting said sample from a patient with a solid support having immobilised thereon a binding agent having binding sites which are capable of specifically binding to said autoantibody under conditions in which said autoantibody binds to the binding agent; and,
    (b) determining the presence or amount of said autoantibody bound to the binding agent.

5. The method of claim 4, wherein step (b) comprises (i) contacting the solid support with a developing agent which is effective to bind to occupied binding sites, unoccupied binding sites or said autoantibody, the developing agent comprising a label and (ii) detecting the label to obtain a value representative of the presence or amount of said autoantibody in said sample.

6. The method of claim 1, wherein the method comprises detecting said autoantibody by Western blot, enzyme-linked immunosorbent assay (ELISA), protein microarray or bead suspension array using purified proteins.

7. The method of claim 6, wherein the protein is immobilised on a solid support.

8. The method of claim 5, wherein the label is a radioactive label, a fluorophor, a phosphor, a laser dye, a chromogenic dye, a macromolecular colloidal particle, a latex bead which is coloured, magnetic or paramagnetic, an enzyme which catalyses a reaction producing a detectable result or the label is a tag.

9. The method of claim 4, which comprises detecting the presence or amount of a plurality of said autoantibodies associated with chronic transplant rejection in a single sample.

10. The method of claim 9, wherein the method employs a plurality of binding agents which are immobilised at predefined locations on the solid support.

* * * * *